(12) United States Patent
Li et al.

(10) Patent No.: US 11,524,279 B1
(45) Date of Patent: Dec. 13, 2022

(54) TRANSITION METAL CARBIDES FOR CATALYTIC METHANE ACTIVATION

(71) Applicants: Iowa State University Research Foundation, Inc., Ames, IA (US); Purdue Research Foundation, West Lafayette, IN (US)

(72) Inventors: Zhe Li, Ames, IA (US); Yue Wu, Ames, IA (US); Arvind Varma, West Lafayette, IN (US); Yang Xiao, West Lafayette, IN (US)

(73) Assignees: Iowa State University Research Foundation, Inc., Ames, IA (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/951,780

(22) Filed: Nov. 18, 2020

Related U.S. Application Data

(60) Provisional application No. 62/937,055, filed on Nov. 18, 2019.

(51) Int. Cl.
*B01J 27/22* (2006.01)
*B01J 23/42* (2006.01)
(Continued)

(52) U.S. Cl.
CPC .............. *B01J 27/22* (2013.01); *B01J 21/063* (2013.01); *B01J 23/28* (2013.01); *B01J 23/42* (2013.01); *B01J 35/0013* (2013.01); *B01J 35/1014* (2013.01); *B01J 35/1038* (2013.01); *B01J 35/1057* (2013.01); *B01J 35/1061* (2013.01); *C07C 2/76* (2013.01); *C07C 5/3337* (2013.01); *C07C 2521/02* (2013.01);
(Continued)

(58) Field of Classification Search
None
See application file for complete search history.

(56) References Cited

U.S. PATENT DOCUMENTS 9,193,595 B2  11/2015  Barsoum et al.
9,415,570 B2   8/2016  Barsoum et al.
(Continued)

OTHER PUBLICATIONS

Anasori et al., Two-dimensional, ordered, double transition metals carbides (MXene), American Chemical Society, 2015, 9, 9507-9516 (Year: 2015).*
(Continued)

*Primary Examiner* — Coris Fung
*Assistant Examiner* — Keling Zhang
(74) *Attorney, Agent, or Firm* — Haukaas Fortius PLLC; Michael H. Haukaas

(57) ABSTRACT

A MXene support for a noble metal that forms a catalyst having active sites comprising single metal-layer nanostructures. The catalyst is stable under conditions for methane conversion to higher hydrocarbons and provides reduced coke formation. The results show a supported metal catalyst using the MXene where Pt atoms form one or more layers of atoms on the surface of the $Mo_2TiC_2T_x$ support after it is reduced at 750° C. The catalyst shows high selectivity for $C_2$-hydrocarbons with reduced coke formation, which can cost effectively convert methane into other valuable products.

20 Claims, 34 Drawing Sheets

(51) Int. Cl.
*B01J 35/00* (2006.01)
*B01J 35/10* (2006.01)
*C07C 2/76* (2006.01)
*C07C 5/333* (2006.01)
*B01J 23/28* (2006.01)
*B01J 21/06* (2006.01)

(52) U.S. Cl.
CPC ...... *C07C 2521/06* (2013.01); *C07C 2523/28* (2013.01); *C07C 2523/42* (2013.01)

(56) References Cited

U.S. PATENT DOCUMENTS

| | | | |
|---|---|---|---|
| 9,416,011 | B2 | 8/2016 | Barsoum et al. |
| 10,967,363 | B1 | 4/2021 | Li et al. |
| 2010/0255983 | A1 | 10/2010 | Zhang |
| 2015/0210044 | A1 | 7/2015 | Barsoum et al. |
| 2016/0336088 | A1 | 11/2016 | Barsoum et al. |
| 2017/0088429 | A1 | 3/2017 | Shin et al. |
| 2017/0294546 | A1 | 10/2017 | Ghidiu et al. |
| 2018/0309125 | A1 | 10/2018 | Beidaghi et al. |
| 2018/0371190 | A1 | 12/2018 | Chopra et al. |
| 2019/0084904 | A1 | 3/2019 | Varma et al. |

OTHER PUBLICATIONS

Anasori et al., "2D Metal Carbides and Nitrides (Mxenes) for Energy Storage," Nat Rev. Mater., 2:1-17, Jan. 2017.

Chen et al., "Catalysts for Steam Reforming of Bio-oil: A Review," Ind Eng Chem Res., 56(16):4627-4637, Apr. 2017.

Ding et al., "A Two-Dimensional Lamellar Membrane: MXene Nanosheet Stacks," Angew Chem Int Ed Engl., 56(7):1825-1829, Feb. 2017.

Gao et al., "Mo2TiC2 MXene: A Promising Catalyst for Electrocatalytic Ammonia Synthesis," Catal Today, 339:120-126, Dec. 2018.

Guo et al., "Direct, Nonoxidative Conversion of Methane to Ethylene, Aromatics, and Hydrogen," Science, 344:616-619, May 2014.

Halim, "Synthesis and Transport Properties of 2D Transition Metal Carbides (MXenes)," Linköping Studies in Science and Technology, Dissertation No. 1953, Oct. 2018; 81 pgs.

Li et al., "Reactive Metal—Support Interactions at Moderate Temperature in Two-Dimensional Niobium-Carbide Supported Platinum Catalysts," Nat Catalysis, 1:349-355, May 2018.

Li et al., "Synthesis and Thermal Stability of Two-Dimensional Carbide MXene Ti3C2," Mater Sci Eng., B, 191:33-40, Jan. 2015.

Naguib et al., "25th Anniversary Article: MXenes: A New Family of Two-Dimensional Materials," Adv Mater., 26(7):992-1005, Feb. 2014.

Naguib et al., "Synthesis of Two-Dimensional Materials by Selective Extraction," Acc Chem Res., 48(1):128-135, Jan. 2015.

Ran et al., "Ti3C2 MXene Co-Catalyst on Metal Sulfide Photo-Absorbers for Enhanced Visible-Light Photocatalytic Hydrogen Production," Nat Comm., pp. 1-10, Jan. 2017.

Wu et al., "Pd—In Intermetallic Alloy Nanoparticles: Highly Selective Ethane Dehydrogenation Catalysts," Catal Sci Technol., 18:6965-6976, Aug. 2016.

Zangeneh et al., "Propane Dehydrogenation over a Commercial Pt—Sn/Al2O3 Catalyst for Isobutane Dehydrogenation: Optimization of Reaction Conditions," Chinese J Chem Eng., 21(7):730-735, Jul. 2013.

Zhang et al., "Single Platinum Atoms Immobilized on an MXene as an Efficient Catalyst for the Hydrogen Evolution Reaction," Nat Catalysis, 1:985-992, Dec. 2018.

Zhang et al., "Synthesis and Charge Storage Properties of Hierarchical Niobium Pentoxide/Carbon/Niobium Carbide (MXene) Hybrid Materials," Chem. Mater., 28(11):3937-3943, May 2016.

Li et al., "Two-dimensional transition metal carbides as supports for tuning the chemistry of catalytic nanoparticles", Nat Comm. 9, Article 5258, pp. 1-8, Dec. 10, 2018.

\* cited by examiner g h («US 11,524,279 B1»)

TRANSITION METAL CARBIDES FOR CATALYTIC METHANE ACTIVATION

RELATED APPLICATIONS

This application claims priority under 35 U.S.C. § 119(e) to U.S. Provisional Patent Application No. 62/937,055, filed Nov. 18, 2019, which is incorporated herein by reference.

BACKGROUND OF THE INVENTION

Inspired by homogeneous catalysts in which each metal atom contributes to a reaction, heterogeneous catalysts have successfully tethered atomically dispersed noble metal (NM) sites on thermally stable solid hosts. Supported atomically dispersed nanolayers (ADNLs) promise to combine the appealing characteristics of single-atom and nanoparticle catalysts: atomically dispersed metal sites that maximize the utilization of NM, anchored on a support through metal-metal bonds at interfaces, leading to metallic surfaces that promote a broad range of reactions such as dehydrogenation, hydrogenation, and oxidation. However, it has proven challenging to prepare ADNLs, i.e., single or double atomic layers, and to relate their structures to catalytic performance. The main barriers arise from difficulty in determining the layer thickness, sintering of active sites at high temperatures (>700° C.), and unpredictable interactions between ADNLs and their supports.

Achieving atomically thin NM architectures in heterogeneous catalysts has long been of interest, with recent progress showing that NMs can wet early transition metal carbide (TMC) surfaces, forming strong interfacial metal-support bonds. For example, raft-like Pt particles were observed in Pt/Mo$_2$C catalysts for the water-gas shift reaction; layered Au clusters coexisted with single Au atoms in Au/α-MoC catalysts; and atomically thin NM monolayers were coated on the surface of tungsten carbide nanoparticles to form core-shell architectures. These advances together with the thermal and chemical stability of TMCs hint that surfaces of group VIB TMCs are ideal for spreading supported NMs, but the interfaces that anchor the nanolayers remain unknown, leading to complexity and uncertainty in understanding the formation and catalytic performance of ADNLs.

The recent boom of shale gas has stimulated renewed interest in C—H bond cleavage as the initial step towards the direct conversion of methane to value-added products. Pt catalysts exhibit satisfactory activity for this chemistry but suffer from rapid deactivation due to coke deposition that covers the active sites. The challenges to achieving stable methane conversion and maintaining activity lie in activating the first C—H bond while inhibiting deep dehydrogenation and persevering highly dispersed active sites at high temperatures (>700° C.).

Accordingly, there is a need for new and improved heterogeneous catalysts for hydrocarbon formation from methane, which catalysts also have high thermal stability and form reduced amounts of side products and coke compared to known catalysts.

SUMMARY

We report that the challenges described above can be met by ADNLs of Pt supported on a two-dimensional (2D) molybdenum-titanium carbide (MXenes). MXene refers to a burgeoning family of 2D metal carbides and nitrides with a general formula of M$_{n+1}$X$_n$T$_x$, where M is an early transition metal, X is carbon and/or nitrogen, and T stands for surface functional groups. We show direct experimental evidence that atomically dispersed Pt nanolayers are anchored on the basal planes of Mo$_2$TiC$_2$T$_x$ MXenes, where the first-layer Pt atoms favorably occupy the HCP sites above the topmost C atoms of the support. Density functional theory (DFT) calculations and in situ spectroscopy suggest that Pt ADNLs are stabilized by Pt—Mo bonding that alters the electronic structure of Pt atoms. The 5d states of the Pt ADNLs are shifted to higher energy, which activate C—H bonds with weaker adsorption of CH$_3$* and thereby suppress coke formation. Consequently, the Pt/Mo$_2$TiC$_2$T$_x$ catalysts delivered stable methane conversion for nonoxidative coupling of methane (NOCM) reactions without deactivation for 72 hours at 750° C. and exhibited >98% selectivity towards ethane/ethylene (C$_2$), with turnover frequencies (TOF) of 0.2-0.6 s$^{-1}$.

Accordingly, this disclosure provides a heterogeneous catalyst comprising an MXene support of Formula I:

$$M_{n+1}X_nT_x \qquad\qquad (I);$$

wherein
each M is independently an early transition metal;
X is a non-metal wherein the non-metal is carbon or nitrogen;
T$_x$ is a surface functional group wherein x is 0-10; and
n is 1, 2, or 3; and
a noble metal atom that occupies a crystal lattice node at the basal plane of the MXene support, wherein the noble metal is supported by a metallic bond to the early transition metal;
wherein the noble metal has one or more nanostructured layers on the MXene support, the one or more nanostructured layers have an average thickness of less than 5 nanometers and loading of the noble metal on the support is less than 5 weight percent.

Also, this disclosure provides a method for converting methane to a hydrocarbon comprising contacting methane and a heterogeneous catalyst described herein, and heating at a temperature greater than 200° C. wherein methane is converted to a saturated or unsaturated (C$_2$-C$_8$)hydrocarbon.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
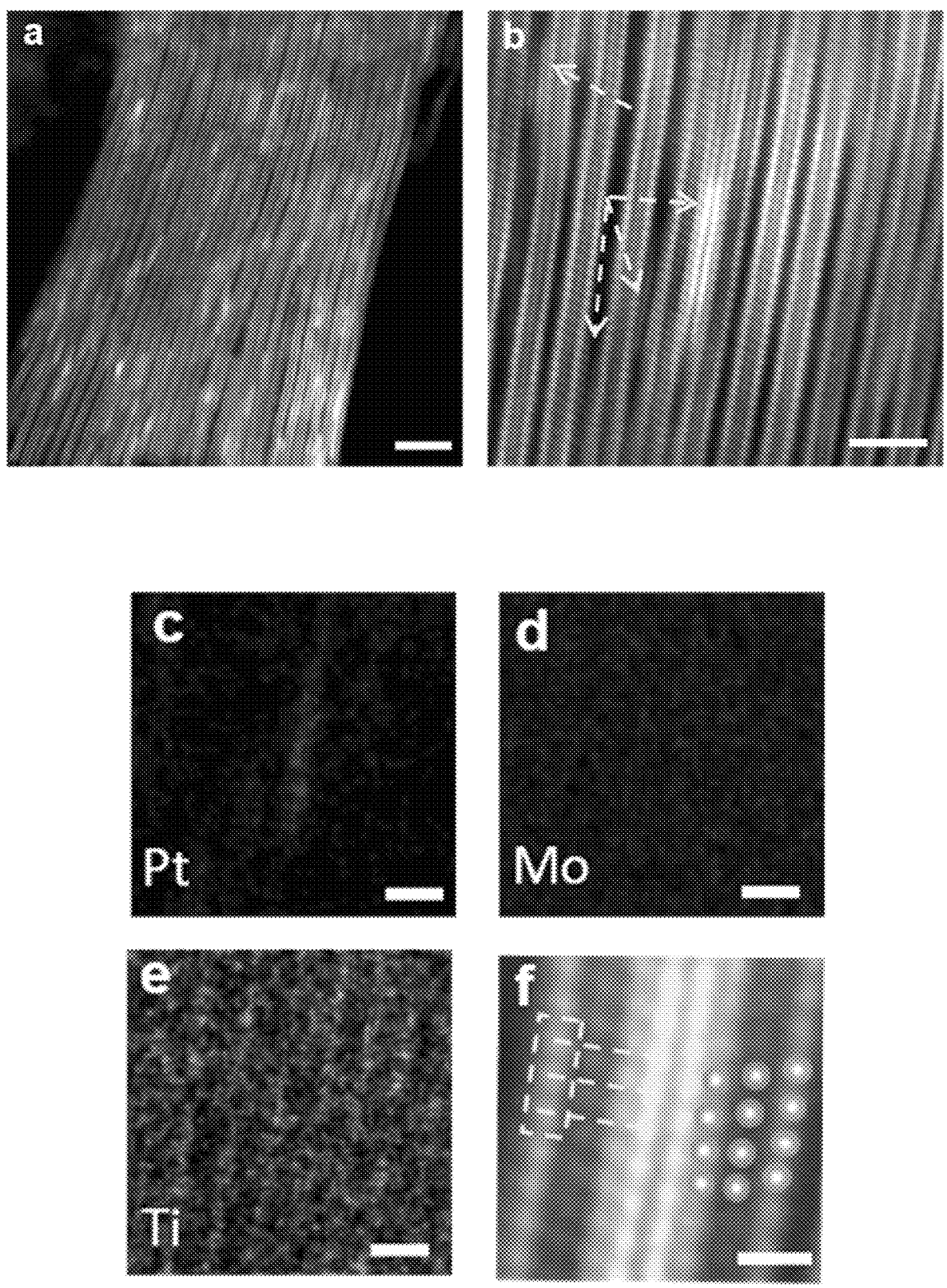
FIG. 1. Atomic structure and DFT calculations of Pt supported by Mo$_2$TiC$_2$T$_x$ MXene. a, HAADF-STEM image of Pt/Mo$_2$TiC$_2$T$_x$ viewed from the [11$\bar{2}$0] direction. Scale bar, 5 nm. b-e, Atomic-resolution HAADF-STEM image showing metal-support interfaces and EDS elemental mappings. ADNLs of Pt are highlighted by yellow arrows in (b). Scale bars, 2 nm. f, Magnified HAADF-STEM image of (b) with metal-support alignment marked by yellow dashed squares and lines. Scale bar 0.5 nm. g,h, HAADF-STEM image viewing from the [0001] direction with its fast Fourier transform pattern shown in the inset (g); image of the Pt monoatomic layer (h). Scale bars, 5 nm (g) and 1 nm (h). i, Relaxed structure showing Pt atoms occupying HCP sites on the surface of $Mo_2TiC_2T_x$ MXene. j, DFT calculated energy per atom of different nanostructured architectures on the surface of $Mo_2TiC_2T_x$ MXene.
Figure 1:
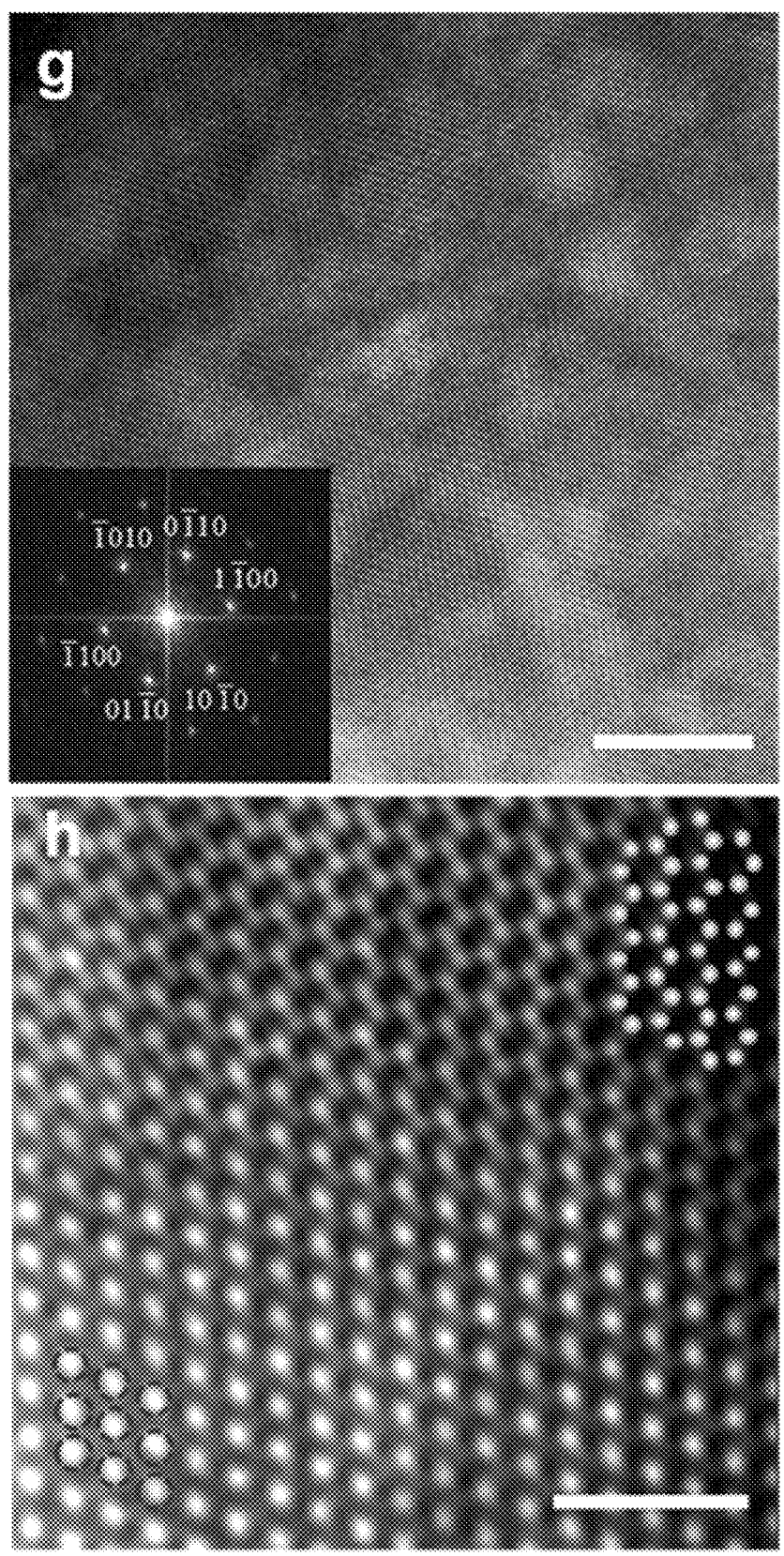
Figure 1:
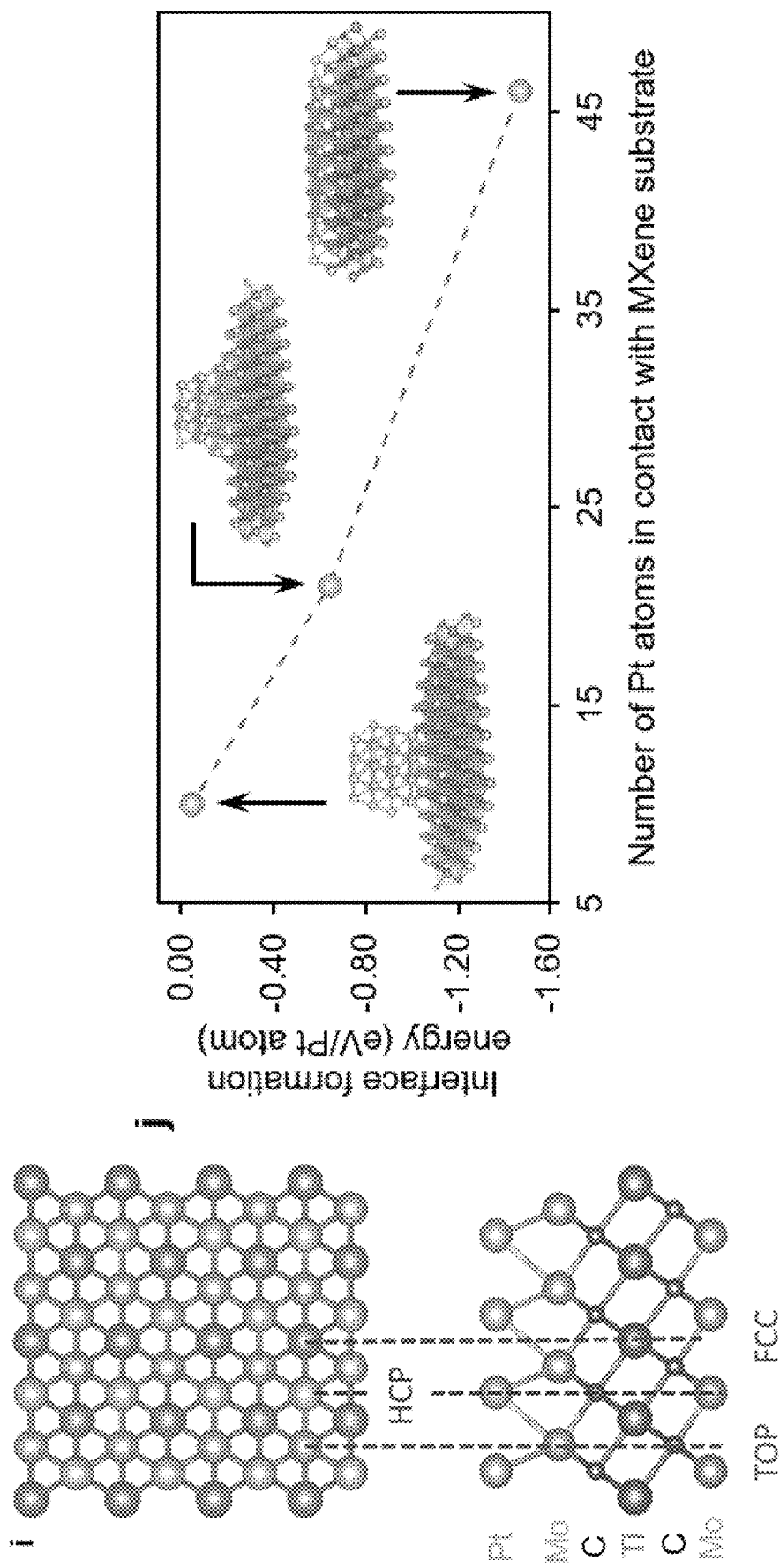

Efficient and direct conversion of methane to value-added products has been a long-term challenge in shale gas applications. Activation of the first C—H bond is essential to methane conversion but is often followed by over-dehydrogenation, leading to coke formation. Here, we show that atomically dispersed nanolayers of Pt with a single or double atomic layer thickness, supported on a two-dimensional molybdenum-titanium carbide (MXene), catalyze nonoxidative coupling of methane to ethane/ethylene ($C_2$). The first-layer Pt atoms favorably occupy the hollow sites (HCP sites) above the topmost C atoms of the MXene support, which are stabilized by Pt—Mo bonds at the metal-support interfaces. Kinetic and theoretical studies reveal that the Pt nanolayers activate the first C—H bond of methane to form methyl radicals that favor desorption over further dehydrogenation and thus suppress coke deposition. At 750° C., the catalyst runs 72 hours of continuous operation without deactivation and exhibits >98% selectivity towards $C_2$ products, with a turnover frequency (TOF) of 0.2-0.6 s$^{-1}$. Our findings provide fundamental understanding of the metal-support interactions between Pt and the surfaces of transition metal carbides and create a new path for developing atomically dispersed supported metal catalysts.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, +10%, +20%, or +25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a chemical reaction, or a physical change, e.g., in a solution, in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. For example, an effective amount of a platinum-transition metal alloy is formed at the surface of a MXene in the catalysts described herein in a sufficient amount to catalyze a conversion reaction. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

Reactive metal support interaction (RMSI) refers to a chemical reaction between a metal and its support that induces the formation of a bimetallic structure. The intermetallic compounds (alloys) described herein are formed due to the RMSI effect.

The term "epitaxy" or "epitaxial" refers to a type of crystal growth or material deposition in which crystalline layers are formed with a well-defined orientation with respect to the substrate (e.g., an MXene). The nanostructured layers formed are called the epitaxial film or epitaxial layer. The relative orientation of the epitaxial layer to the substrate is defined in terms of the orientation of the crystal lattice. For epitaxial growth, the new layer will be crystalline, and will all have a single orientation relative to the substrate. For example, layers of platinum atoms form a nanostructure wherein the atoms are oriented epitaxially.

Embodiments of the Invention

This disclosure provides a heterogeneous catalyst comprising an MXene support of Formula I:

$$M_{n+1}X_nT_x \qquad (I);$$

wherein
each M is independently an early transition metal;
X is a non-metal wherein the non-metal is carbon or nitrogen;
$T_x$ is a surface functional group wherein x is 0-10; and
n is 1, 2, or 3; and
a noble metal atom that occupies a crystal lattice node at the basal plane of the MXene support, wherein the noble metal is supported by a metallic bond to the early transition metal;
wherein the noble metal has one or more nanostructured layers on the MXene support, the one or more nanostructured layers have an average thickness of less than 5 nanometers and loading of the noble metal on the support is less than 5 weight percent.

In some embodiments, the occupied crystal lattice node is a hexagonal close packed (HCP) crystal lattice node. In some embodiments, the non-metal occupies another crystal lattice node between the early transition metal and a different second early transition metal that occupies a third crystal lattice node. In some embodiments, the non-metal is positioned beneath the early transition metal.

In some embodiments, the average thickness is about 0.3 nanometer to about 2.0 nanometers. In various embodiments, the noble metal is oriented epitaxially in the one or more nanostructured layers. In various embodiments, the one or more nanostructured layers are layered epitaxially. In various embodiments, the noble metal forms nanostructures that are layered or oriented epitaxially. In various embodiments, the noble metal nanostructures are ordered or arranged epitaxially, the noble metal nanostructures have an ordered arrangement or pattern, or the noble metal nanostructures have a crystalline arrangement or pattern. In various embodiments, the noble metal nanostructures have a structured arrangement, orientation, or pattern. In various embodiments, the noble metal nanostructures are layered in a structured arrangement, orientation, or pattern.

And/or, in various embodiments the noble metal is atomically dispersed and structured as one layer of atoms, two layers of atoms, three layers of atoms, four layers of atoms, five layers of atoms, 6-10 layers of atoms, 11-25 layers of atoms, 26-50 layers of atoms, 51-100 layers of atoms or 101-1000 or more layers of atoms.

In other embodiments, the loading is about 0.1 weight percent to about 2.5 weight percent. In additional embodiments, the loading is about 0.1 weight percent to about 1.0 weight percent. In yet other embodiments, the noble metal is platinum, iridium, rhodium, palladium, or a combination thereof. In other embodiments, the noble metal is replaced with bismuth, antimony, or a combination thereof.

In some other embodiments, x is 1-10 and the surface functional group is halo, hydroxyl, oxo, or a combination thereof. In yet other embodiments, M is hafnium, niobium, molybdenum, titanium, tungsten, tantalum, vanadium, zirconium, or a combination thereof. In additional embodiments, X is carbon and n is 1 or 2. In other embodiments, the MXene support is $Mo_2TiC_2T_x$. In further embodiments, the catalyst is about 0.1-0.8 wt % $Pt/Mo_2TiC_2T_x$ or about 0.8-2.2 wt % Pt/Mo$_2$TiC$_2$T$_x$. In other embodiments, the loading of platinum on the MXene support is about 0.1 wt % to about 5 wt % Pt/Mo$_2$TiC$_2$T$_x$, or about 0.1 wt % to about 2 wt % Pt/Mo$_2$TiC$_2$T$_x$.

In some embodiments, a platinum atom occupies an HCP crystal lattice node at the basal plane of the MXene support, the platinum atom is supported by a metallic bond to a molybdenum atom, a carbon atom occupies another crystal lattice node between the molybdenum atom and a titanium atom that occupies a third crystal lattice node, and the carbon atom is positioned beneath the molybdenum atom. In other embodiments, the titanium atom is between two molybdenum atoms, and the titanium atom is distanced from the two molybdenum atoms by carbon atoms.

This disclosure also provides a method for converting methane to a hydrocarbon comprising contacting methane and the heterogeneous catalyst described herein, and heating at a temperature greater than 200° C. wherein methane is converted to a saturated or unsaturated (C$_2$-C$_8$)hydrocarbon.

In some embodiments, formation of petroleum coke is less than 30 milligrams per gram catalyst when the heating is for 72-hours or less. In additional embodiments, a C$_2$-hydrocarbon is formed at greater than 80% selectivity. In yet other embodiments, methane conversion to the (C$_2$-C$_8$) hydrocarbon is greater than 5%. In various embodiments, the catalyst is 0.1-0.8 wt % Pt/Mo$_2$TiC$_2$T$_x$ or 0.1-0.8 wt % Pt/Mo$_2$TiC$_2$T$_x$. In other embodiments, heating is at a temperature of about 200° C. to about 800° C.

In other embodiments, contacting is at a gas hourly space velocity (GHSV) of about 4 h$^{-1}$ to about 14 h$^{-1}$ and at a temperature of about 600° C. to about 900° C. In yet other embodiments, a C$_2$-hydrocarbon is formed at greater than 80% selectivity and at a turnover frequency of greater than 0.1 s$^{-1}$.

In various embodiments, the catalysts have high rates and stability, and they operate at very high temperature without loss of activity. Current catalysts are typically over-reduced and permanently lose activity at similar high temperatures. Compared to other catalysts, the platinum MXene catalysts described herein have higher rates, longer life, and form less carbon, which is a significant problem for reactions at high temperature. The catalysts can be drop-in replacements with superior performance to current catalysts.

The platinum loading of the catalyst can be about 0.5 wt. % to about 20 wt. %. In various embodiments, the platinum loading of the catalyst can be about 1% to about 20%, about 1% to about 10%, about 1% to about 5%, or less than about 5%. In one specific embodiment, the platinum loading of the catalyst is about 1-2%.

The percentage of exposed platinum of the catalyst can be about 1-8% or about 3-5% of the platinum loading, by weight. The platinum dispersion can be greater than about 1%, greater than about 10%, or preferably greater than about 50%.

The catalyst can have an average particle size of about 0.5 nm to about 20 nm. In various embodiments, the average particle size is about 1 nm to about 10 nm, about 1 nm to about 5 nm, or about 2 nm to about 3 nm. In various embodiments, the average particle size of the catalyst can be about 1-3 nm, about 2 nm to about 3.2 nm, or about 2.6 nm.

The catalyst can include a suitable inert support such as a silica support.

In various embodiments, the catalyst maintains a carbide, nitride, or carbonitride nanosheet structure after reduction by hydrogen gas at 550° C.

In various embodiments, the temperature can be at least about 250° C., at least about 280° C., at least about 300° C., or about 250° C. to about 350° C.

In various embodiments, the pressure of the reaction is less than 100 atmospheres and greater than 1 atmosphere. Thus, the pressure of the reaction can be less than about 100 atmospheres, less than about 50 atmospheres, and preferably less than about 20 atmospheres.

Additionally, this disclosure provides a method for converting methane to a hydrocarbon comprising contacting methane and a heterogeneous catalyst comprising:

a MXene support of Mo$_2$TiC$_2$T$_x$ and platinum metal atomically dispersed as one or more nanostructured layers (or as a single nanostructured layer) on the MXene support, wherein the one or more layers has an average thickness of less than 5 nanometers and the loading of the platinum metal on the support is less than 5 weight percent; and heating at a temperature greater than 200° C. wherein methane is converted to a saturated or unsaturated (C$_2$-C$_8$)hydrocarbon.

In other various embodiments the platinum nanostructures are dispersed as one layer (or as a single layer) on the MXene support. In various embodiments, the platinum nanostructures are layered or oriented epitaxially. And/or, in various embodiments the platinum nanostructures are atomically dispersed as one layer of atoms, two layers of atoms, three layers of atoms, four layers of atoms, five layers of atoms, 6-10 layers of atoms, 11-25 layers of atoms, or 26-50 layers of atoms.

Results and Discussion

Figure 5:
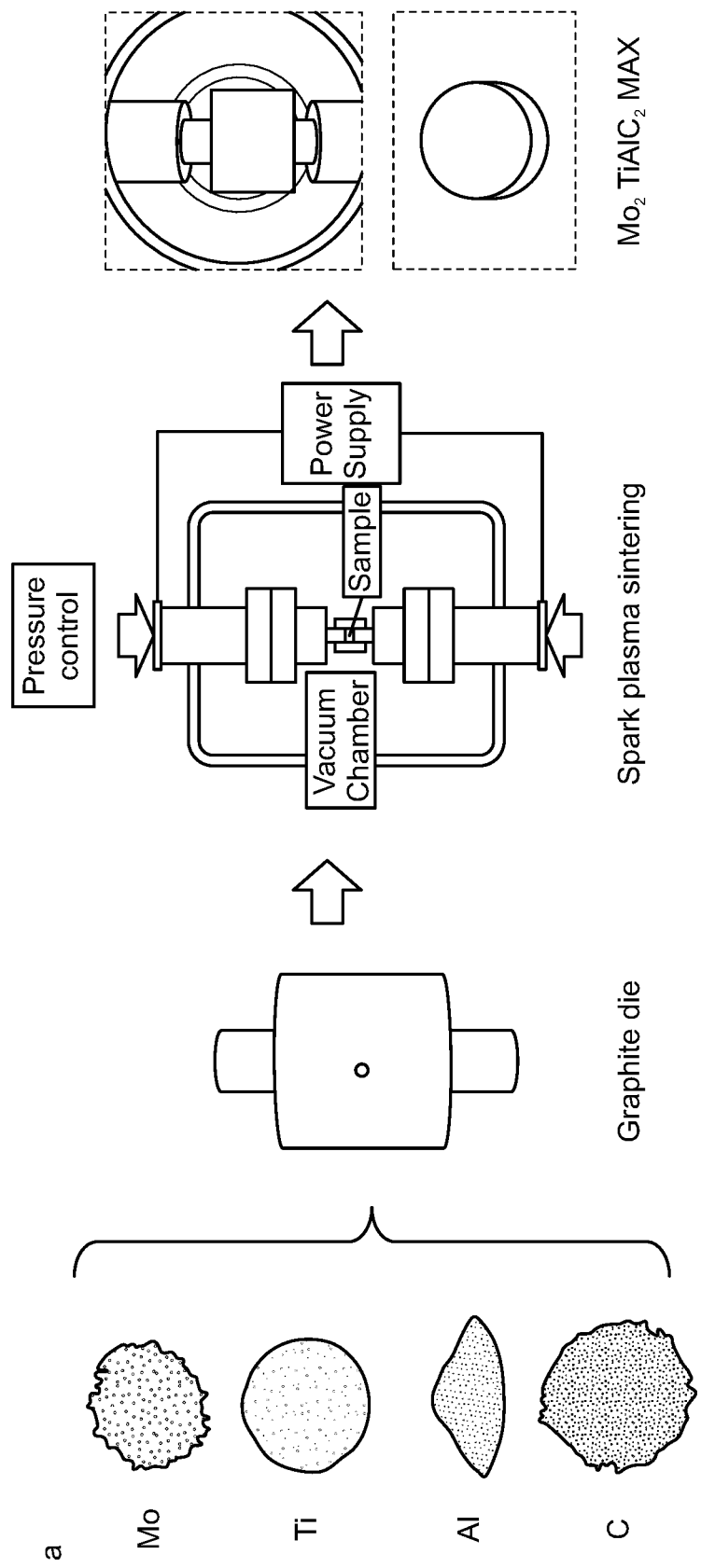
FIG. 5. Schematic of $Mo_2TiC_2T_x$ MXene preparation (a) Synthesis of $Mo_2TiAlC_2$ MAX using spark plasma sintering (SPS). (b) Preparation of $Mo_2TiC_2T_x$ MXene by HF treatment.
Figure 5:
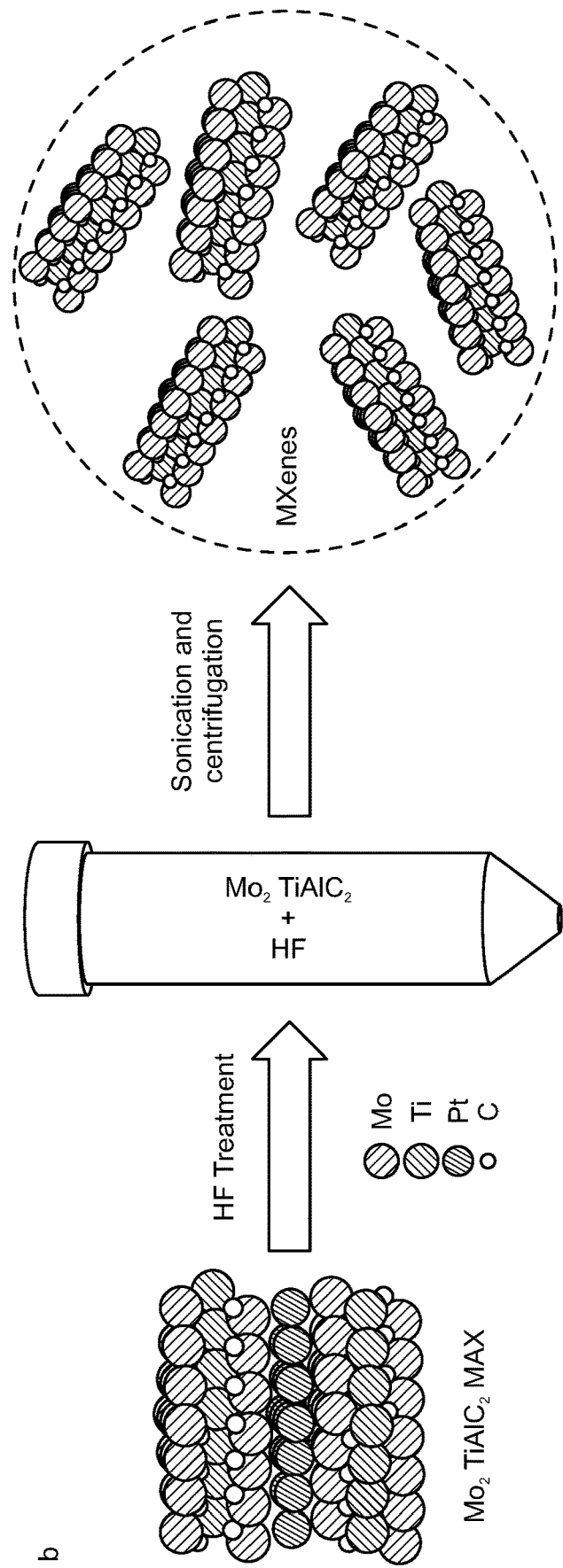

Structural characterizations of atomically dispersed platinum nanolayers. To prepare Pt/Mo$_2$TiC$_2$T$_x$ catalysts, a quaternary TMC (MAX), i.e., Mo$_2$TiAlC$_2$, was synthesized by solid-state sintering, followed by HF etching to remove Al and obtain the layered Mo$_2$TiC$_2$T$_x$ MXene (FIG. 5). Pt was loaded on Mo$_2$TiC$_2$T$_x$ MXene by incipient-wetness impregnation (IWI), which was activated at 450° C. for NOCM (see details in Example). Aberration-corrected high-angle annular dark-field scanning transmission electron microscopy (HAADF-STEM) was employed to investigate the activated catalyst at atomic resolution and to identify metal-support interfaces. The HAADF-STEM images viewed along the [11$\overline{2}$0] zone axis confirm the atomic ordering of the Mo$_2$TiC$_2$T$_x$ support, where a layer of Ti is sandwiched between two Mo layers (FIG. 1a,b). The brighter atoms exhibited higher Z-contrast than the underlying Mo MXene support (FIG. 1b), corresponding to Pt bilayers that intercalated between two layers of Mo$_2$TiC$_2$T$_x$ MXene. Energy dispersive X-ray spectroscopy (EDS) elemental mappings (FIG. 1c-e) also confirm that Pt wets the surface of the MXene support. This result differs from that of Pt supported on other transition metal surfaces, such as Pt/Ti$_3$C$_2$T$_x$ and Pt/Nb$_2$CT$_x$, where Pt alloyed with surface transition metals and formed intermetallic nanoparticles upon in situ co-reduction. This difference suggests that the formation of atomic-layered Pt is not due to the spatial confinement of MXene layers but rather to Mo surfaces and their interactions with Pt.

FIG. 1f shows the direct imaging of Pt—Mo MXene interfaces, indicating that the Pt atoms at the bottom layer preferentially occupy the HCP sites, i.e., positions of the bottom Mo layer (marked as yellow dashed square) on the surface of Mo$_2$TiC$_2$T$_x$ MXene. These results suggest that Pt strongly interacts with the Mo$_2$TiC$_2$T$_x$ MXene with a large interfacial adhesion energy and that the growth of Pt nanolayers is dictated by metal-support bonding instead of surface energies, i.e., Wulff theorem (*ChemCatChem*, 2011, 3, 934).

Figure 6:
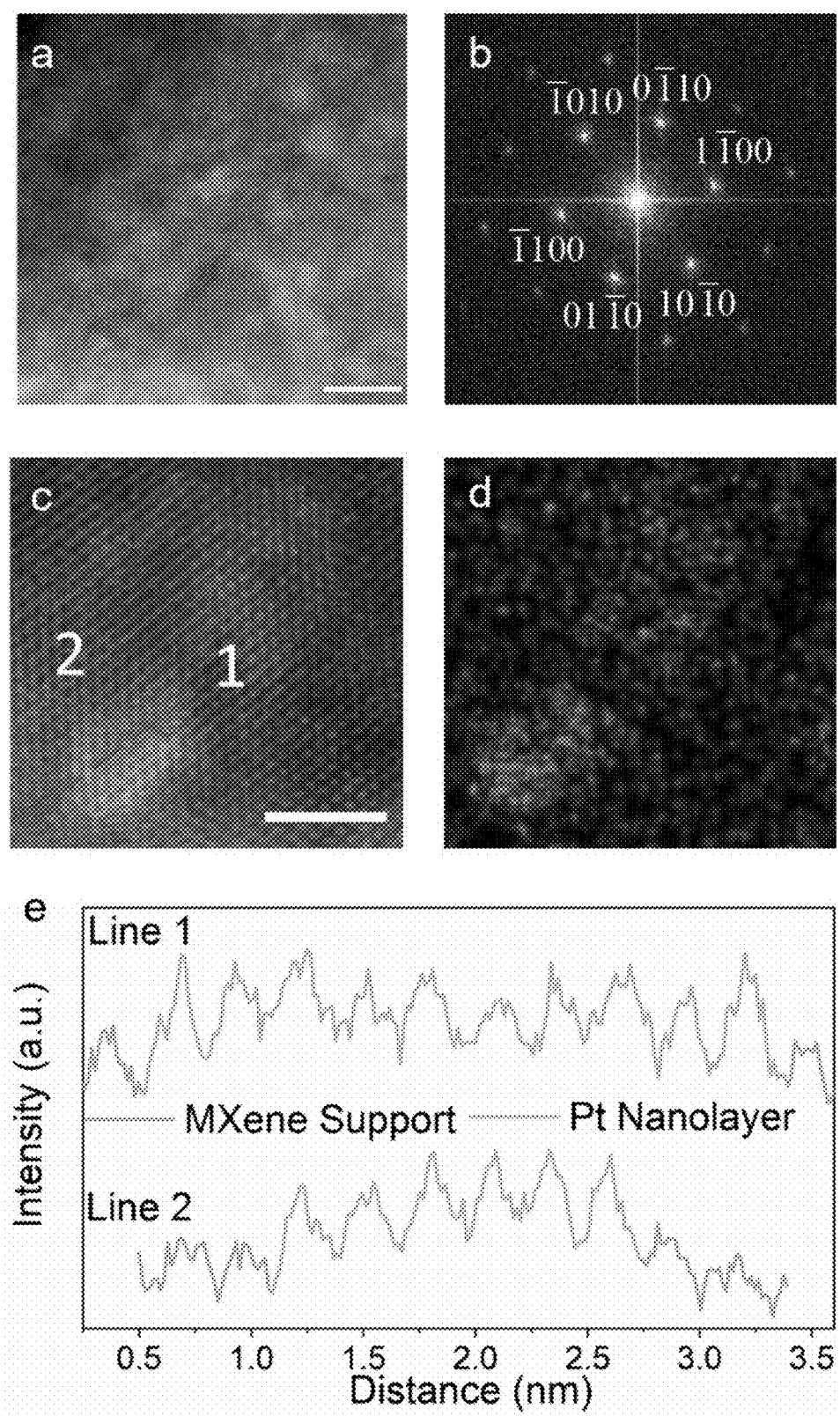
FIG. 6. (a) STEM image of 0.5% $Pt/Mo_2TiC_2T_x$ reduced at 450° C. viewing from [0001] direction, Scale bar 5 nm. (b) fast Fourier transform pattern of (a). (c) HAADF-STEM image of a Pt ADNLs on the surface of $Mo_2TiC_2T_x$ MXene. Scale bar 2 nm. (d) EDS elemental mapping of (c). (e) Integrated pixel intensities of Pt NL (taking from the pink dash lines in c). The lattice spacing measured from the image (2.80 Å) can be assigned to Pt {110} planes, indicating that the epitaxial Pt nanolayer strongly aligns with the MXene support.
Figure 7:
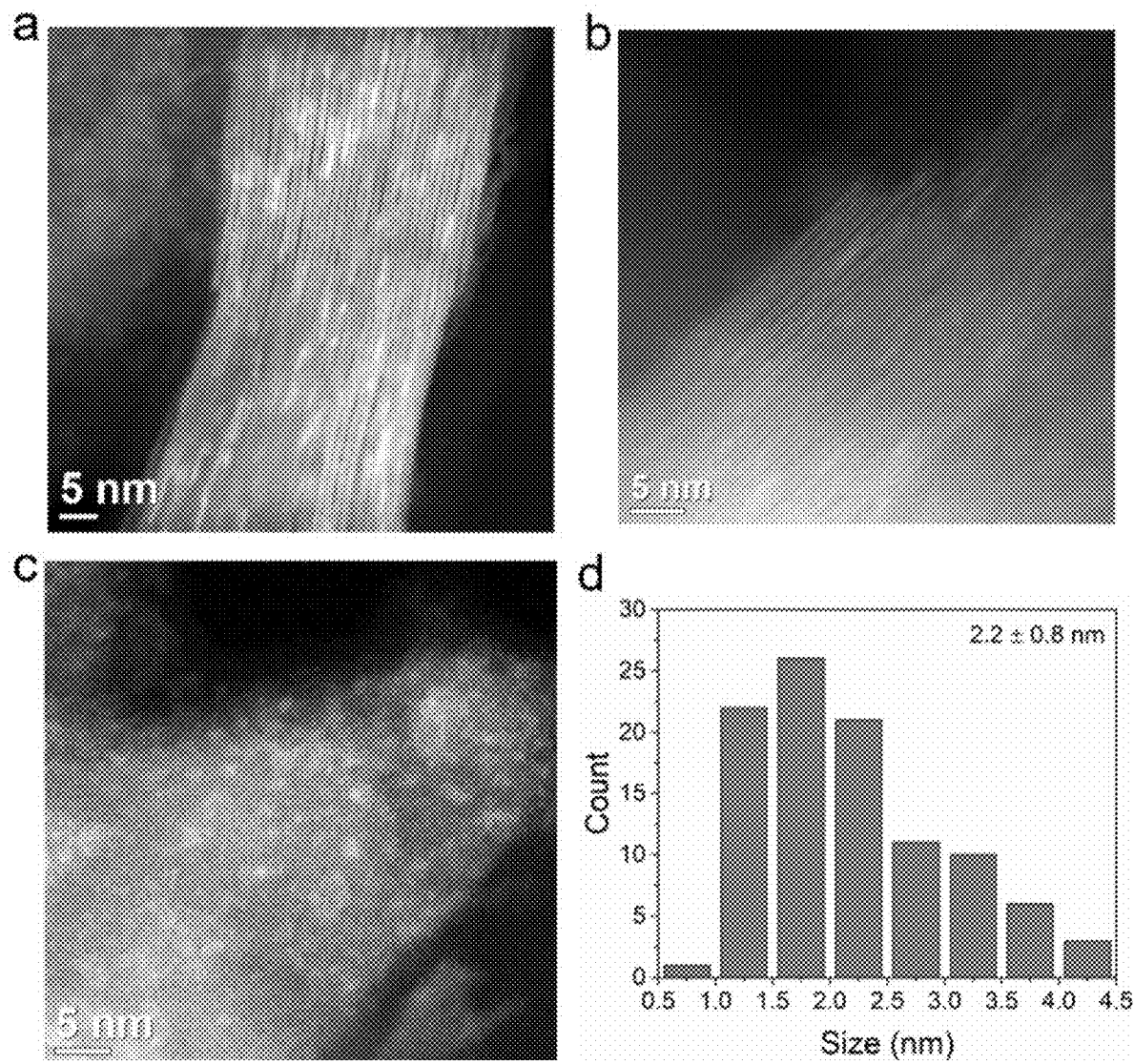
FIG. 7. (a-c) HAADF-STEM overview image of $Pt/Mo_2TiC_2T_x$ catalysts reduced at 450° C. (d) Size distribution of more than 100 nanolayers. The average size of the nanolayers is 2.2 nm.

HAADF-STEM imaging of the basal plane ([0001] direction) of Pt/Mo$_2$TiC$_2$T$_x$ provided further evidence for the formation of Pt nanolayers on the MXene support (FIG. 1g). The characteristic hexagonal pattern of Mo$_2$TiC$_2$T$_x$ (marked by blue atoms) is accompanied by regions of enhanced Z-contrast corresponding to Pt atoms (bottom left corner of FIG. 1h). The Pt atoms are situated on HCP sites of the surface of Mo$_2$TiC$_2$T$_x$ MXene, forming rhombic patterns (marked by red circles) that are characteristic of Pt monolayers (FIG. 1i). The single Pt layers maximize the atom efficiency by exposing all atoms on their surface, leading to ~100% dispersion. Moreover, continuous lattice fringes across the metal-support interfaces were observed (Figure if), indicating epitaxial growth of the Pt nanolayers on the Mo$_2$TiC$_2$T$_x$ MXene. Detailed crystal structure analysis (FIG. 6 and FIG. 7) showed that epitaxial Pt nanolayers with an average size of ~2.2 nm aligned their (111) planes with the (0001) planes of the MXene support, leading to an epitaxial relationship of [111]Pt/[0001] Mo$_2$TiC$_2$T$_x$ MXenes.

Figure 8:
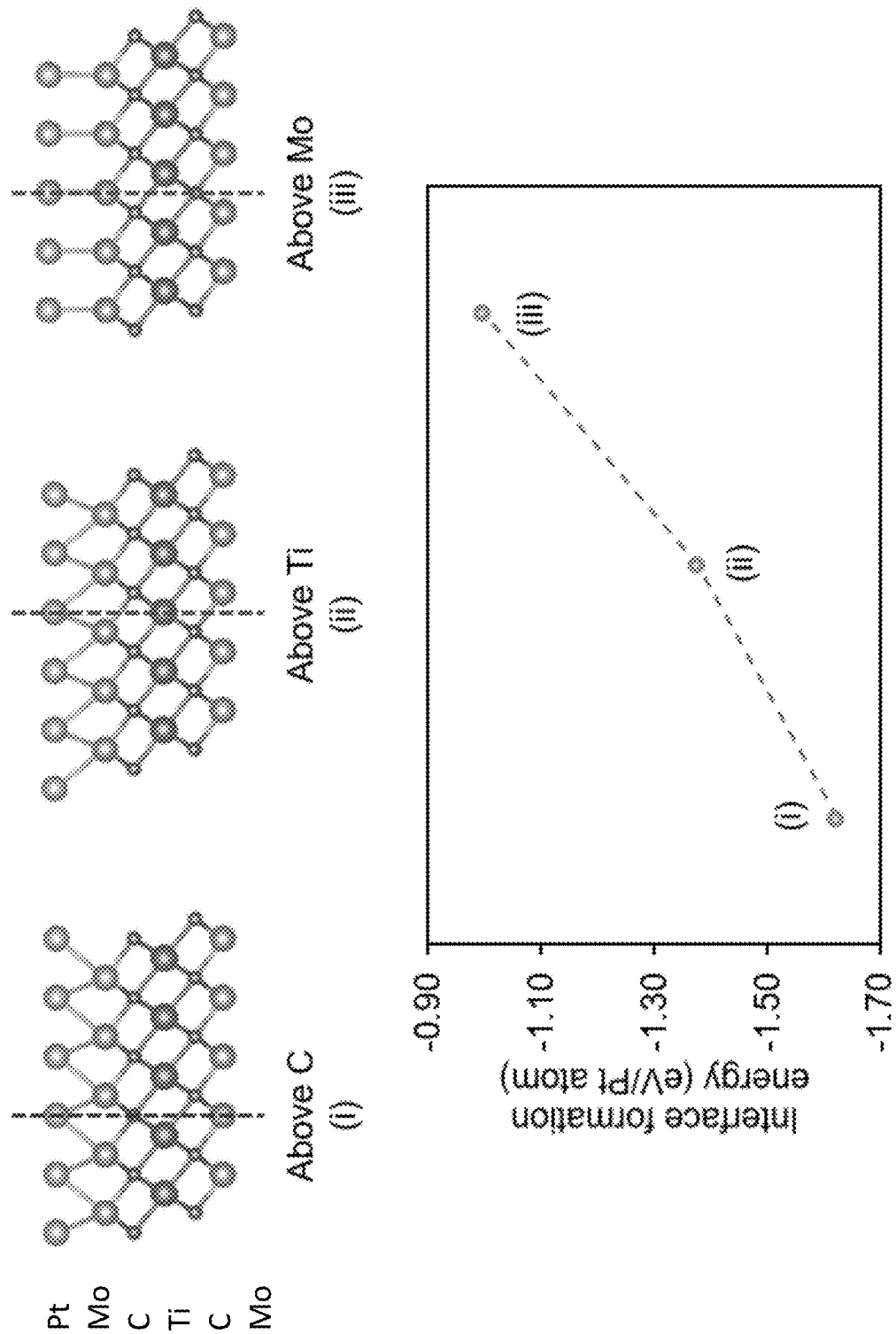
FIG. 8. DFT calculated interface formation energies of Pt atoms on HCP, FCC and atop sites of $Mo_2TiC_2T_x$ surface. Pt (red), Mo (blue), Ti (green) and C (black).

Our experimental results suggest that the chemisorption of Pt atoms on the HCP sites of the MXene support through metal-support bonding can account for the formation of atomically dispersed Pt nanolayers. DFT calculations were thus performed to assess the interface formation energies (see Example for details) of Pt by three different sites on the basal plane of Mo$_2$TiC$_2$T$_x$ MXene: Mo atop sites, FCC sites and HCP sites (FIG. 1i). When Pt is coordinated on an HCP site (FIG. 1i), the binding of Pt is more favored (−1.62 eV/Pt atom) than the weaker adsorption on the FCC (−1.38 eV/Pt atom) and Mo atop (−1.00 eV/Pt atom) sites (FIG. 8). FIG. 1j shows the calculated interface formation energies for Pt nanolayers and nanoparticles along with the structures in the inset figures. We found that the atomically dispersed Pt monolayer is the most stable structure with the lowest energy compared to the nanoparticle structures. Moreover, a comparison of the two nanoparticle geometries shows that with a decrease in the number of interfacial Mo—Pt bonds, the energy of the system increases, further illustrating the preference of Pt atoms to form single or double atomically dispersed layers with a maximum number of Pt atoms bonded to the MXene surface, rather than nanoparticle or nanopillar type structures where more Pt—Pt bonds are formed.

Figure 2:
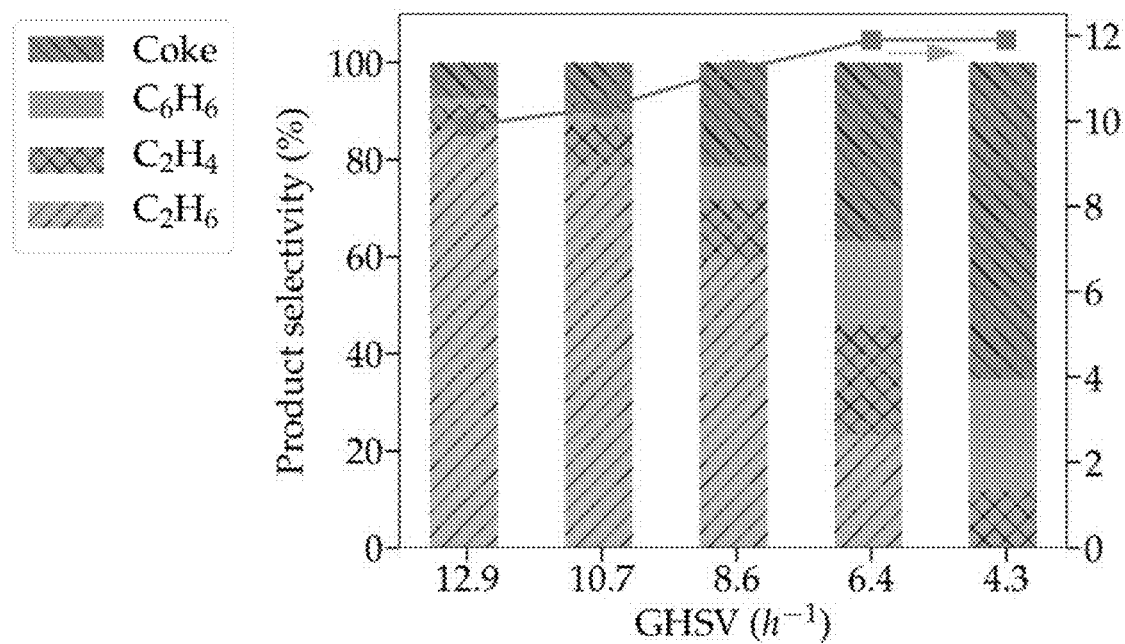
FIG. 2. Catalytic performance of $Pt/Mo_2TiC_2T_x$ for nonoxidative coupling of methane. a-c, 2% Pt (a), 1% Pt (b), and 0.5% Pt (c) over MXene, respectively, at 750° C. in the GHSV range of 4.3-12.9 $h^{-1}$. d,e, Plots of $C_2$ selectivity (d) and TOF (e) vs methane conversion under the same conditions as (a-c). f, TPSR over 0.5% Pt/MXene at GHSV 8.6 $h^{-1}$.
Figure 2:
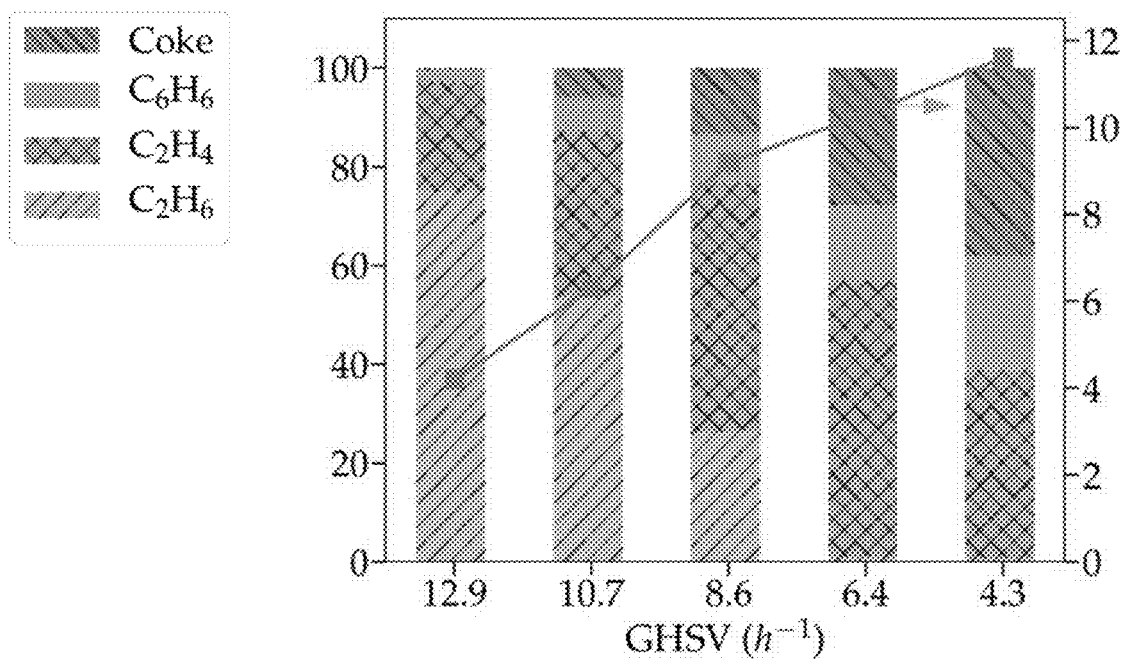
Figure 2:
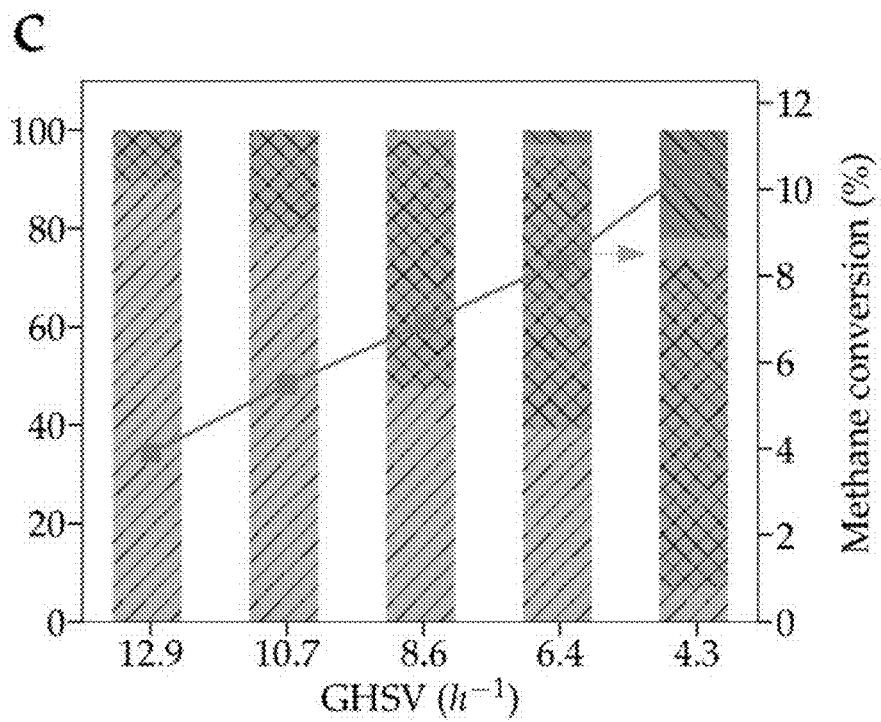
Figure 2:
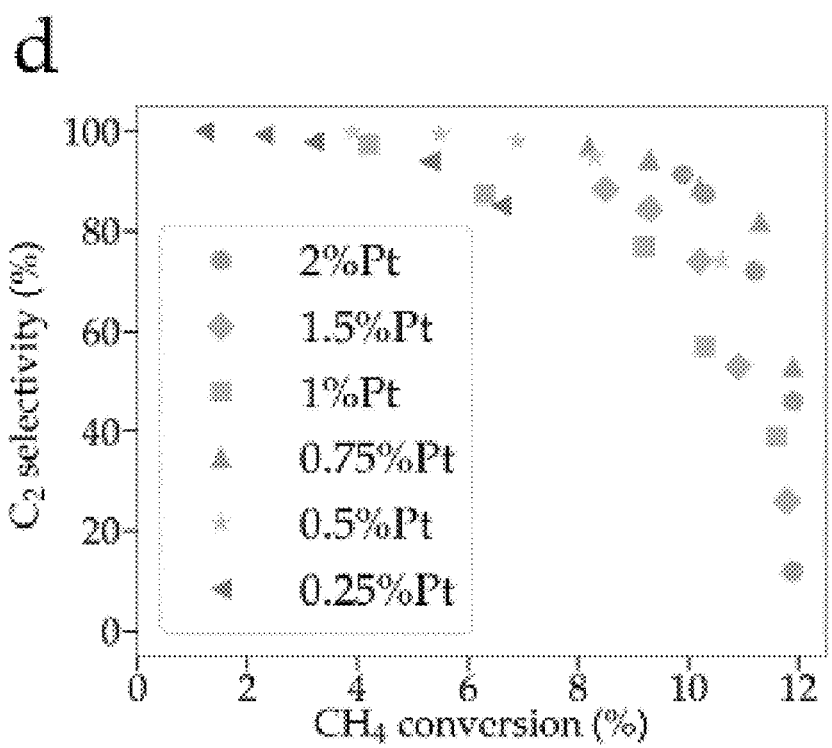
Figure 2:
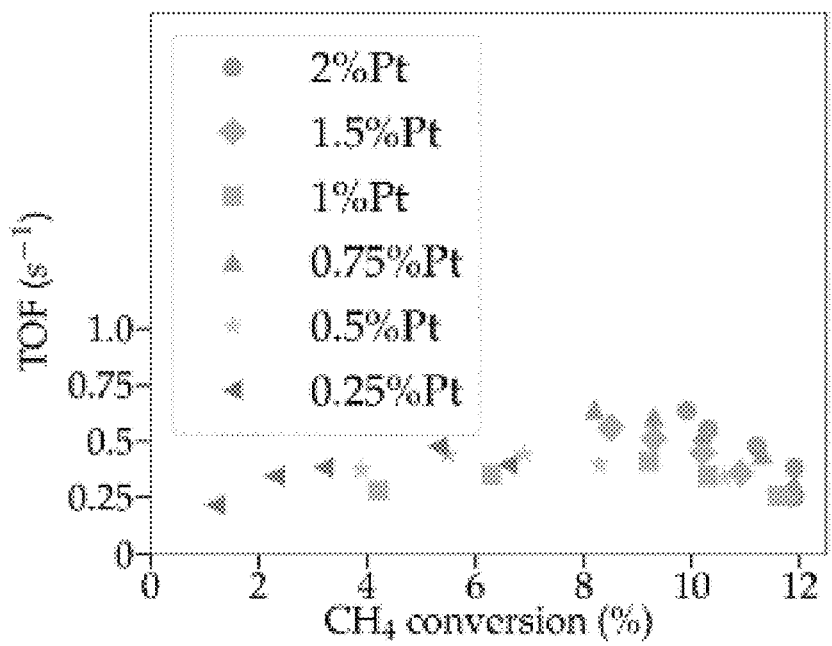
Figure 2:
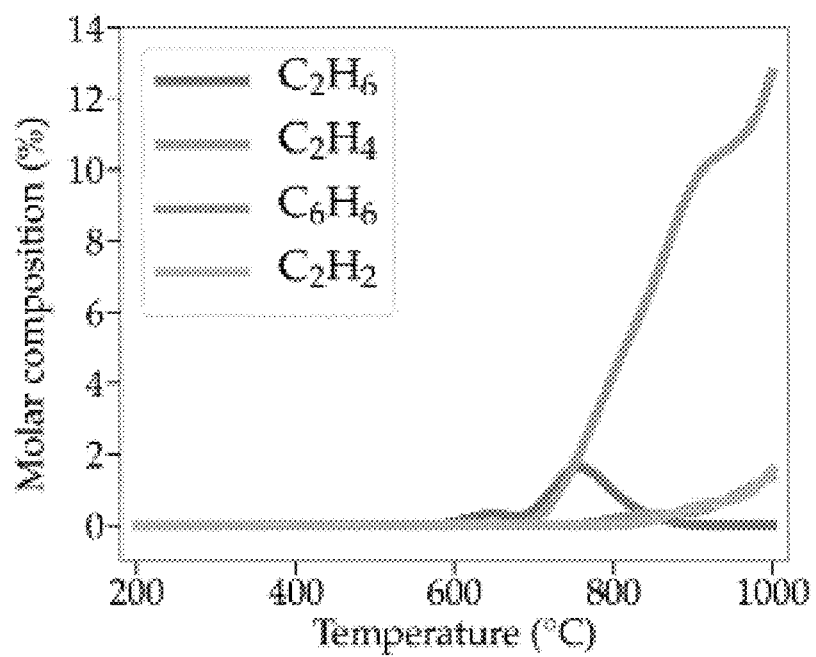
Figure 9:
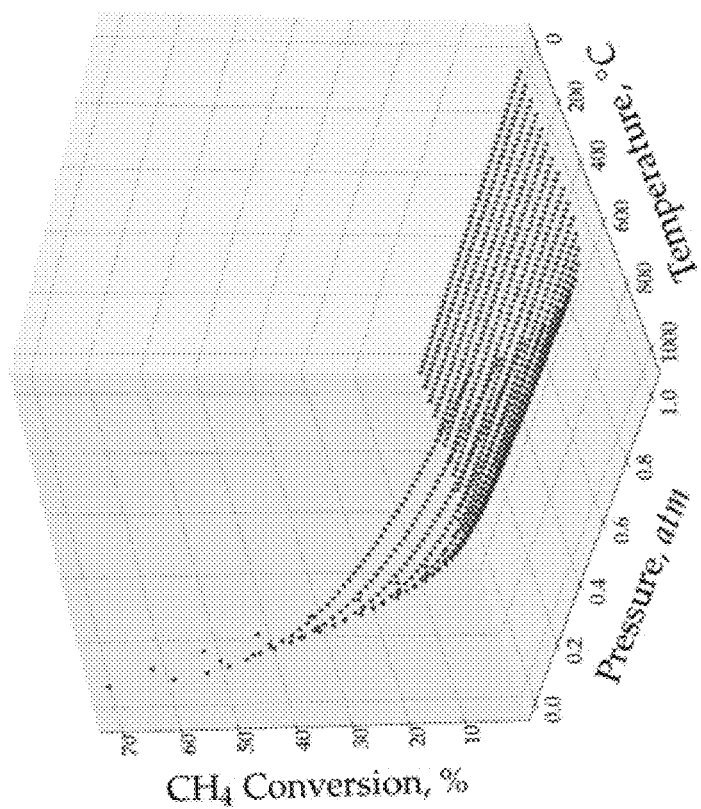
FIG. 9. Effects of temperature and partial pressure on equilibrium methane conversion for ethane (a) and ethylene formation (b).
Figure 9:
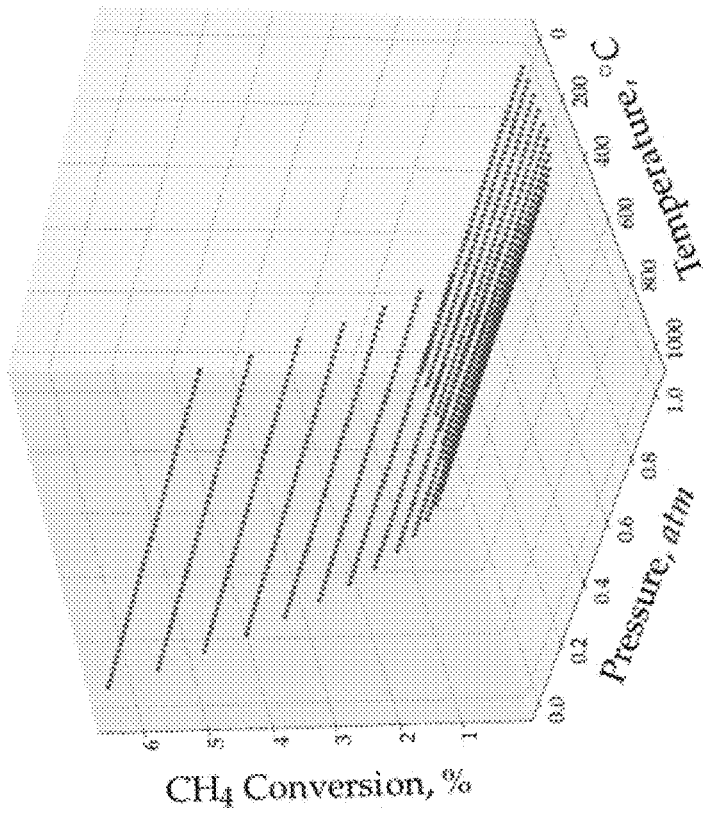
Figure 10:
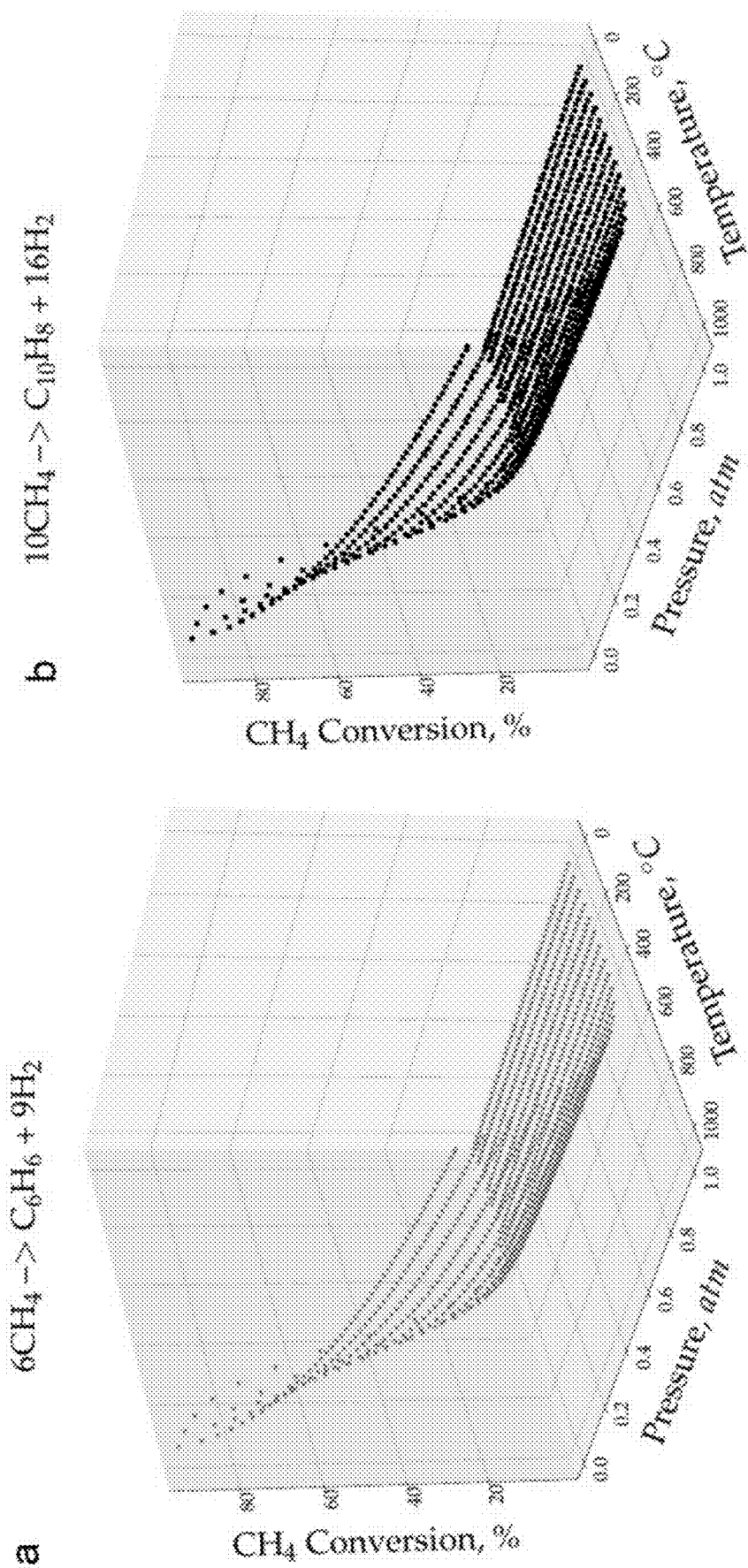
FIG. 10. Effects of temperature and partial pressure on equilibrium methane conversion for benzene (a) and naphthalene (b) formation.
Figure 11:
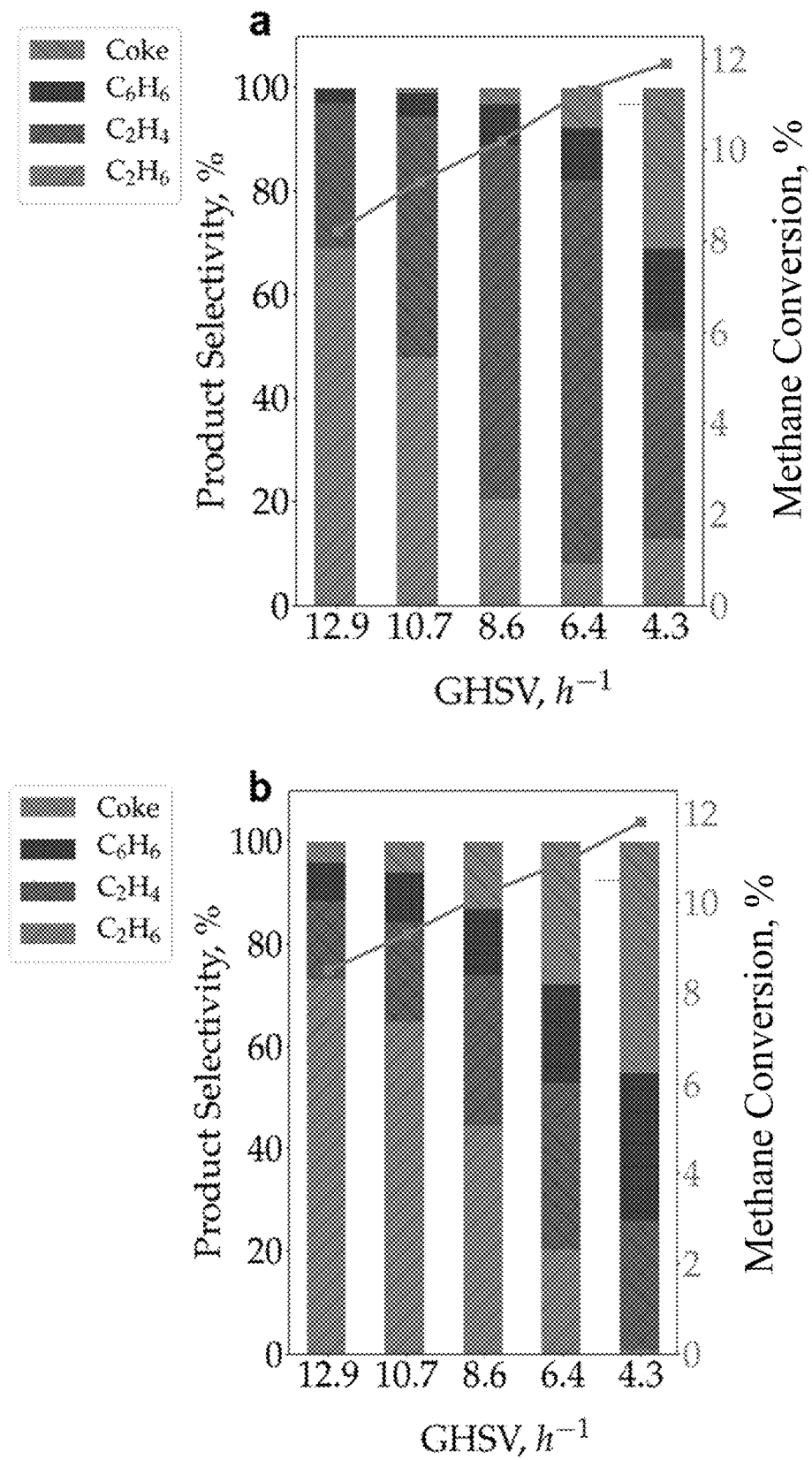
FIG. 11. Catalytic performance of 0.25% (a), 0.75% (b) and 1.5% (c) Pt/MXene catalysts for nonoxidative coupling of methane, at 750° C. in GHSV (gas hourly space velocity) range 4.3-12.9 $h^{-1}$.
Figure 11:
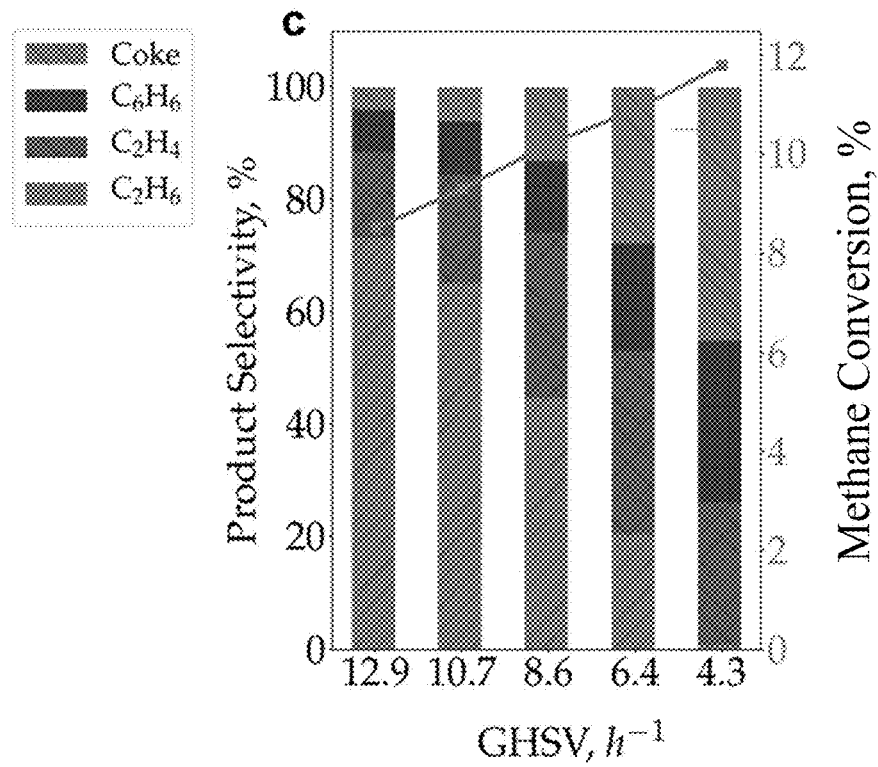

Catalytic performance of Pt/Mo$_2$TiC$_2$T in NOCM In a flow fixed-bed reactor, NOCM was performed over various Pt/Mo$_2$TiC$_2$T$_x$ catalysts with different Pt loadings (i.e., 2%, 1.5%, 1%, 0.75%, 0.5% and 0.25%; see Table 1 for details), as shown in FIG. 2a-c. These catalysts exhibited a surface area of 26-33 m$^2$/g, a pore size of ~3 nm and a pore volume of 0.05-0.08 cm$^3$/g (Table 2) and showed minimum loss of Pt metal during the reactions (Table 1). Thermodynamically, both a low methane pressure and a high operating temperature promote the formation of desired ethane/ethylene (FIG. 9), as well as undesired coke precursors (FIG. 10). From a kinetically perspective of the series of reactions converting methane to ethane/ethylene followed by benzene/naphthalene, the effect of gas hourly space velocity (GHSV) was investigated in FIG. 2a-c and FIG. 11. Methane conversion increased with decreasing GHSV for all catalysts. Both high Pt loading and low GHSV contributed to coke accumulation, resulting in rapid deactivation of the catalysts. Among all tested catalysts, the 0.5% Pt/Mo$_2$TiC$_2$T$_x$ catalyst exhibited the best coke-resistant property at 8.6-12.9 h$^-$ GHSV, 750° C., 30.5-60.5% methane conversion and >98% selectivity to C$_2$ species.

FIG. 2d shows the relation between methane conversion and C$_2$ selectivity. High C$_2$ selectivity was typically obtained at low methane conversion over low-Pt-loading catalysts. The 0.5% Pt/Mo$_2$TiC$_2$T$_x$ catalyst remained >95% selective towards C$_2$ species at a methane conversion of 8%, while other catalysts showed either lower methane conversion or lower selectivity towards C$_2$. The Pt dispersion, i.e., the ratio of the number of surface atoms to the number of total atoms, was measured by the H$_2$—O$_2$ titration method (see Example), which was employed to normalize all methane conversion rates to obtain the turnover frequency (TOF) (FIG. 2e). The Pt dispersions were determined to be 91%, 65% and 34% for 0.5% Pt/Mo$_2$TiC$_2$T$_x$, 1% Pt/Mo$_2$TiC$_2$T$_x$, and 2% Pt/Mo$_2$TiC$_2$T$_x$, respectively (Table 3). Increasing the Pt loading from 0.25% to 2% substantially decreases the Pt dispersions (from 97% to 34%) in Pt/Mo$_2$TiC$_2$T$_x$ catalysts, suggesting that three-dimensional (3D) Pt nanoparticles or nanoflakes that promote coke deposition start to form at higher Pt loadings (>0.5%). The dispersions of low Pt loading catalysts (0.25% and 0.5%) are close to 100%, indicating the formation of ADNLs, which is consistent with the results of HAADF-STEM and DFT calculations. It should be noted that all these TOF values fell within a relatively narrow range (0.2-0.6 s$^{-1}$), implying similar activity of the surface Pt atoms for NOCM in all Pt/Mo$_2$TiC$_2$T$_x$ catalysts. To our best knowledge, the TOFs of Pt/Mo$_2$TiC$_2$T$_x$ are among the highest values for methane activation, compared with the values of 0.0005-0.05 s$^{-1}$ in the literature (*ACS Catal.* 2018, 8, 4044).

TABLE 1

ICP-AES elemental analysis for various Pt/MXene catalysts.

| target catalyst[1] | fresh catalyst, Pt % by ICP[2] | spent catalyst, Pt % by ICP[2] |
|---|---|---|
| 2.0% Pt | 1.91 | 1.88 |
| 1.5% Pt | 1.44 | 1.39 |
| 1.0% Pt | 0.93 | 0.89 |
| 0.75% Pt | 0.75 | 0.75 |
| 0.5% Pt | 0.47 | 0.46 |
| 0.25% Pt | 0.23 | 0.21 |

[1]The Pt weight percentage is based on the amount used in catalyst preparation procedure.
[2]The Pt weight percentage refers to the actual value measured by ICP-AES analysis. The spent catalysts were tested for 8-hour runs.

Figure 3:
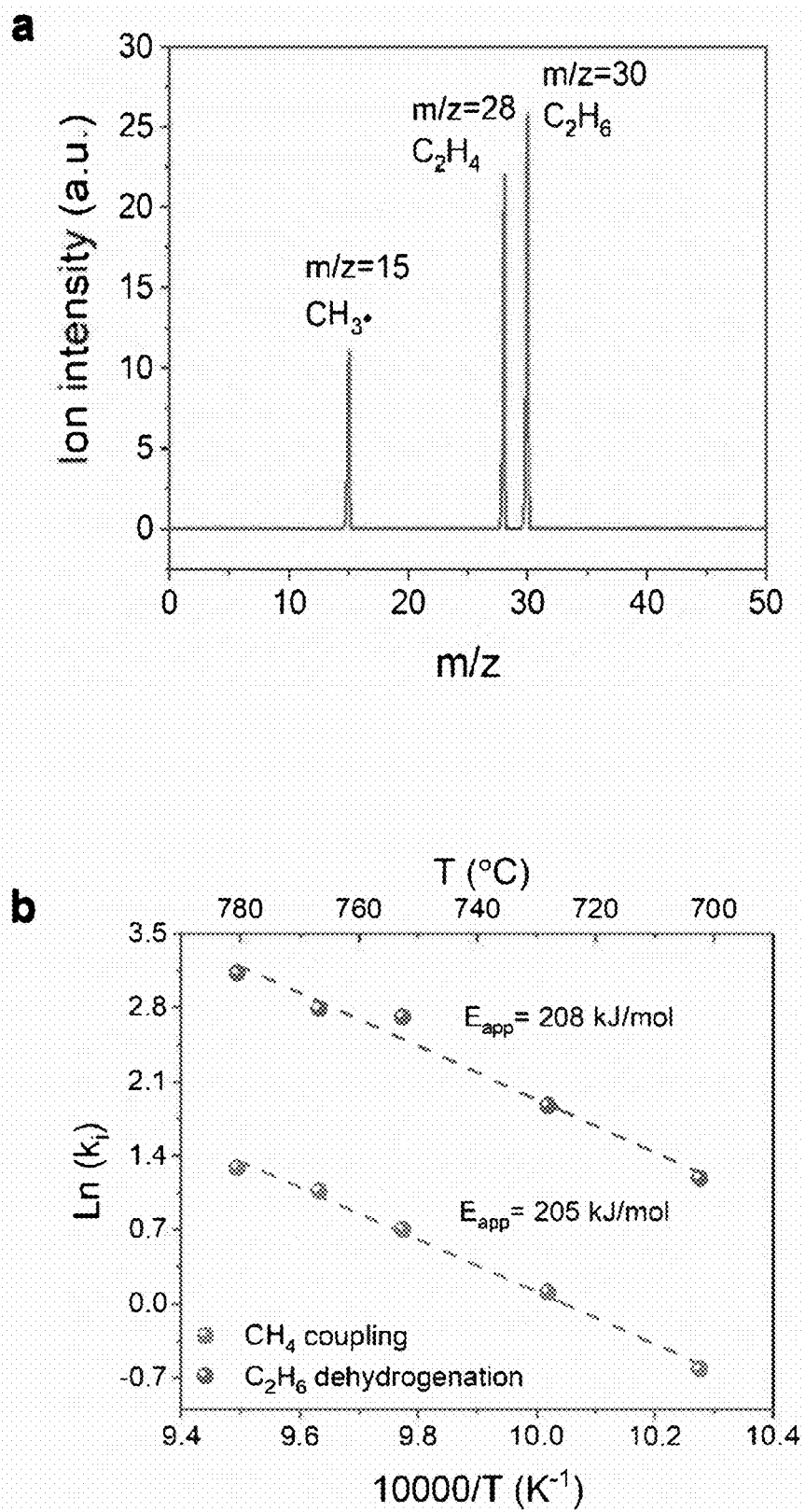
FIG. 3. Kinetics studies and stability characterizations. a, Mass spectrum of a sample obtained at the reactor outlet over 0.5% $Pt/Mo_2TiC_2T_x$ at GHSV 8.6 $h^{-1}$ and 750° C. b, Arrhenius plots for the rate constants of methane coupling and ethane dehydrogenation. c, Long-term catalyst stability of 0.5% $Pt/Mo_2TiC_2T_x$ at 750° C. and GHSV 8.6 $h^{-1}$. d, In situ Pt $L_{III}$ edge XANES spectra of $Pt/Mo_2TiC_2T_x$ reduced at 750° C. compared to Pt foil. e, In situ magnitude of the Fourier transform of the $k^2$ weighted EXAFS spectra of $Pt/Mo_2TiC_2T_x$ reduced at 750° C. compared to Pt foil. f, HAADF-STEM image of 0.5% $Pt/Mo_2TiC_2T_x$ reduced at 750° C. viewed from the [0001] direction. The inset shows the corresponding fast Fourier transform pattern. Scale bar, 5 nm. g,h, HAADF-STEM image and EDS elemental mapping of Pt ADNLs on the surface of $Mo_2TiC_2T_x$ MXene. Scale bar, 1 nm.
Figure 3:
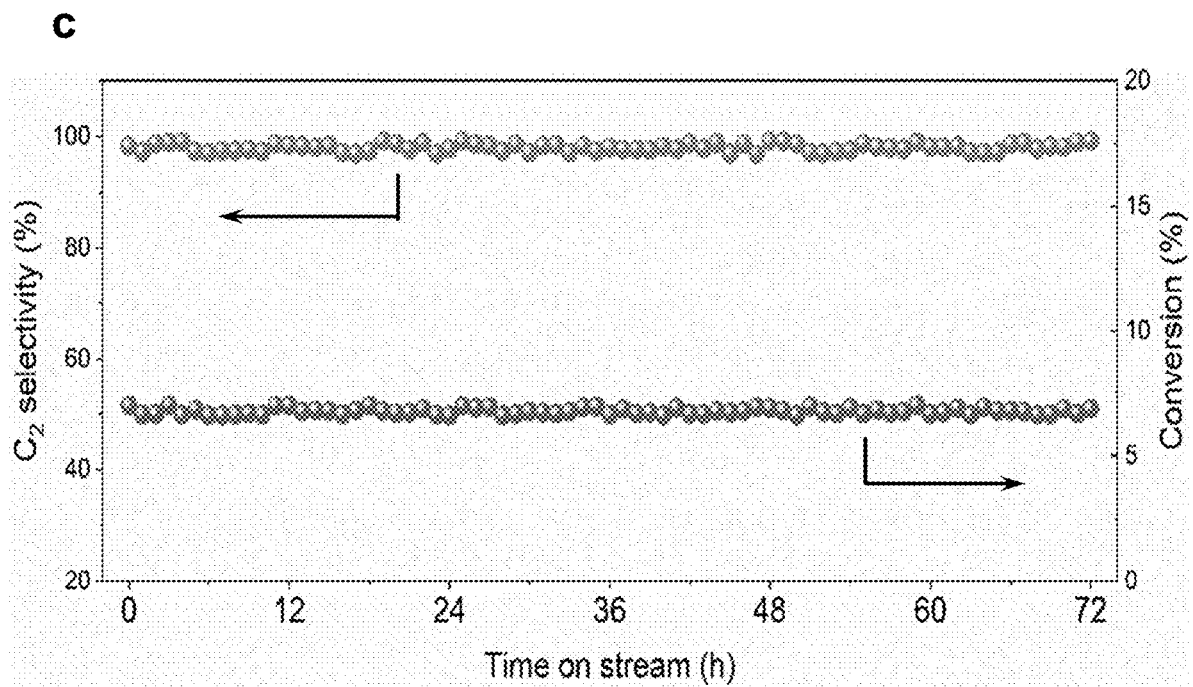
Figure 3:
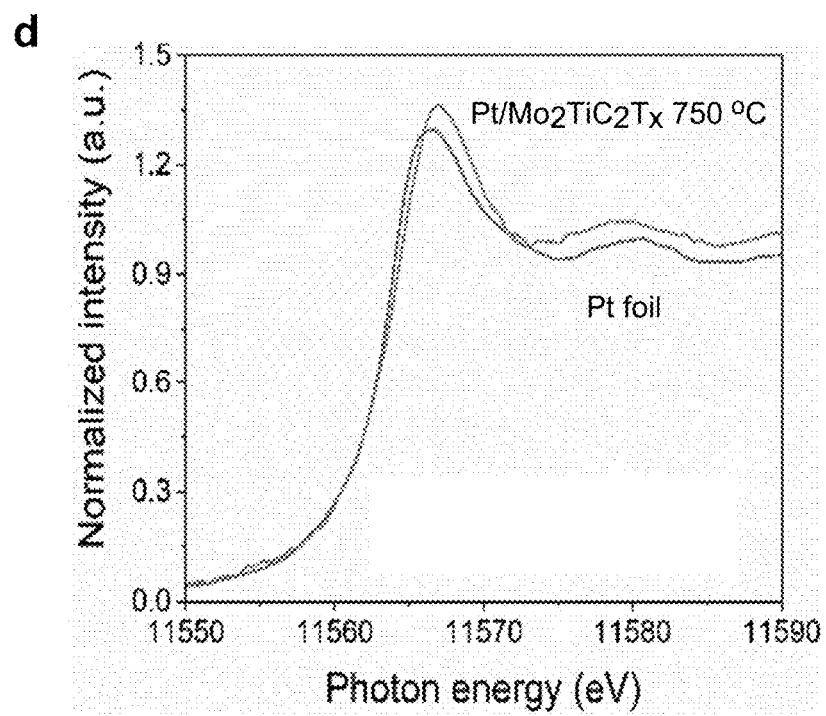
Figure 3:
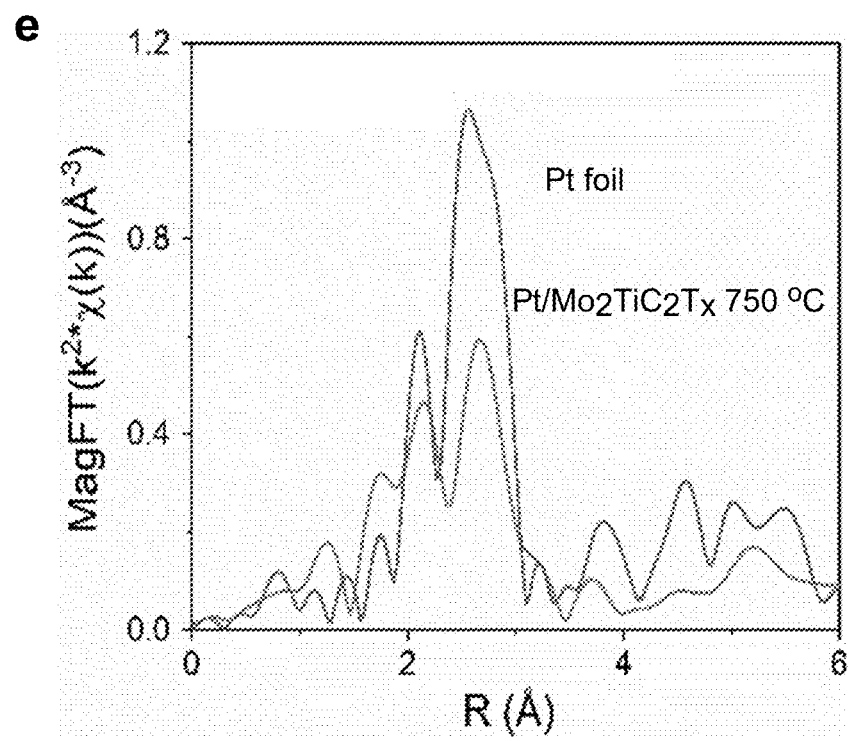
Figure 3:
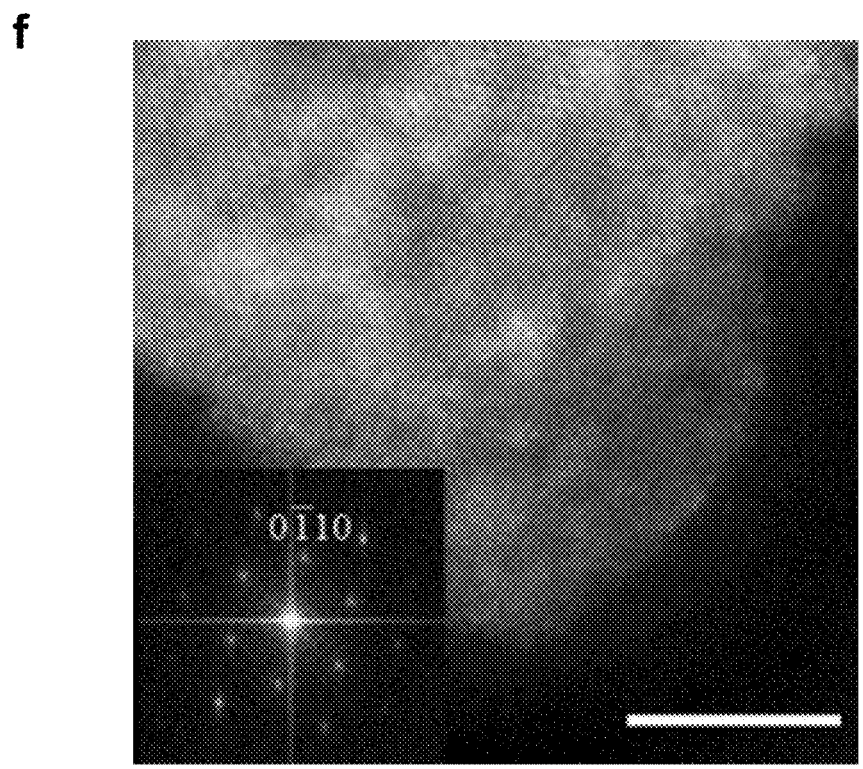
Figure 3:
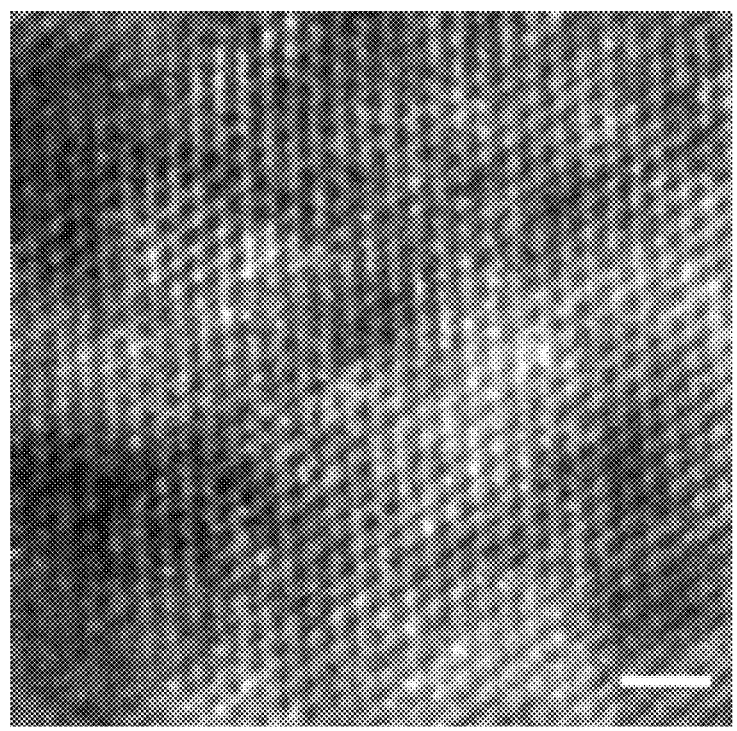
Figure 3:
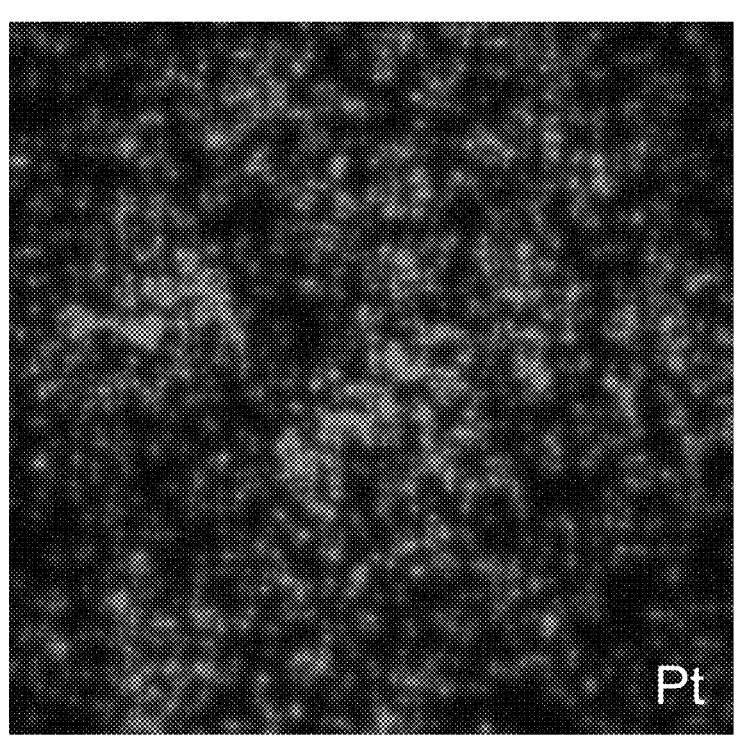

Temperature-programmed surface reaction (TPSR) was carried out over 0.5% Pt/Mo$_2$TiC$_2$T$_x$ to investigate the effect of the operating temperature on product distribution. As shown in FIG. 2f, methane was not efficiently activated until 600° C. At 600-700° C., a trace amount of ethane was found as the only product, while at 700-800° C., both ethane and ethylene were generated from methane coupling. Trace amounts of acetylene (C$_2$H$_2$) and benzene were also detectable as byproducts. At higher operating temperatures (>800° C.), ethane dehydrogenation led to more ethylene as well as undesired acetylene and benzene (coke precursors), rapidly deactivating the catalyst. FIG. 3a presents the mass spectrum of a sample obtained at the reactor outlet. In addition to ethane (m/z=30) and ethylene (m/z=28), methyl radicals (m/z=15) were also detected. The presence of methyl radicals as an intermediate suggests that the ADNLs activate the first C—H bond of methane to form methyl radicals and two methyl radicals in the gas-phase couple to form an ethane molecule that is further dehydrogenated to ethylene. A similar reaction mechanism was also observed in previous NOCM catalysts (Science 2014, 344, 616).

TABLE 2

BET results for Pt-based catalysts supported on MXene.

| Catalyst (wt %) | BET Surface Area, m²/g | Pore Size, nm | Pore Volume, cm³/g |
|---|---|---|---|
| 2.0% Pt | 26.6 | 2.9 | 0.06 |
| 1.5% Pt | 28.6 | 3.3 | 0.07 |
| 1.0% Pt | 29.1 | 3.1 | 0.05 |
| 0.75% Pt | 32.9 | 3.5 | 0.06 |
| 0.5% Pt | 31.2 | 3.1 | 0.08 |
| 0.25% Pt | 29.4 | 3.4 | 0.06 |
| unsupported MXene | 31.7 | 3.2 | 0.07 |

Figure 12:
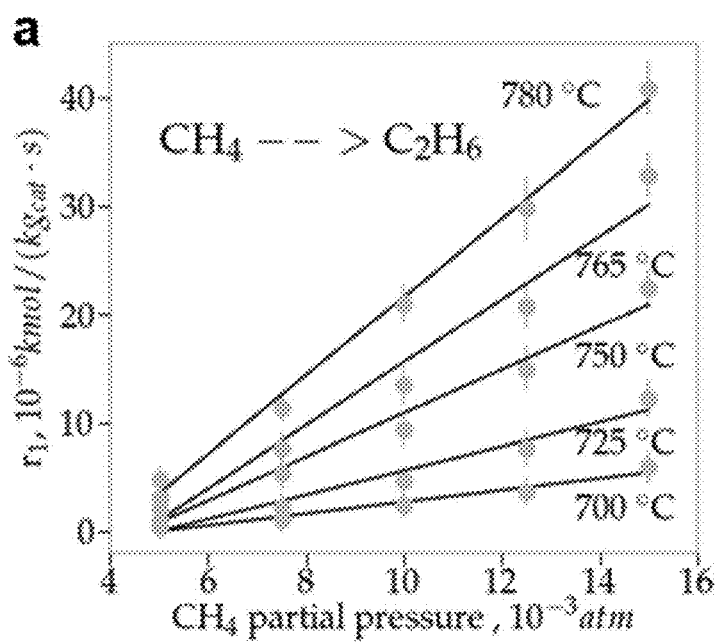
FIG. 12. Kinetic fittings of methane coupling (a) and ethane dehydrogenation (b) over 0.5% Pt/MXene at GHSV 8.6 $h^{-1}$.
Figure 12:
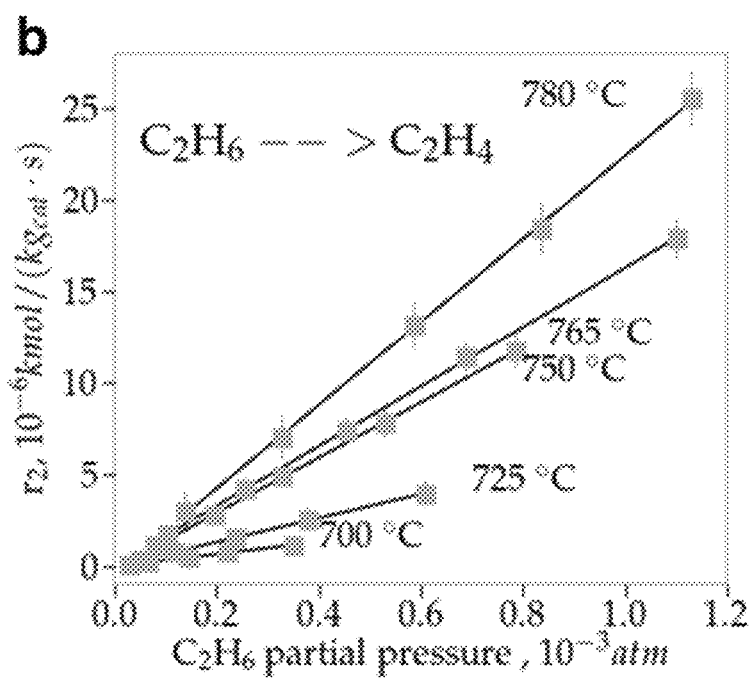
Figure 13:
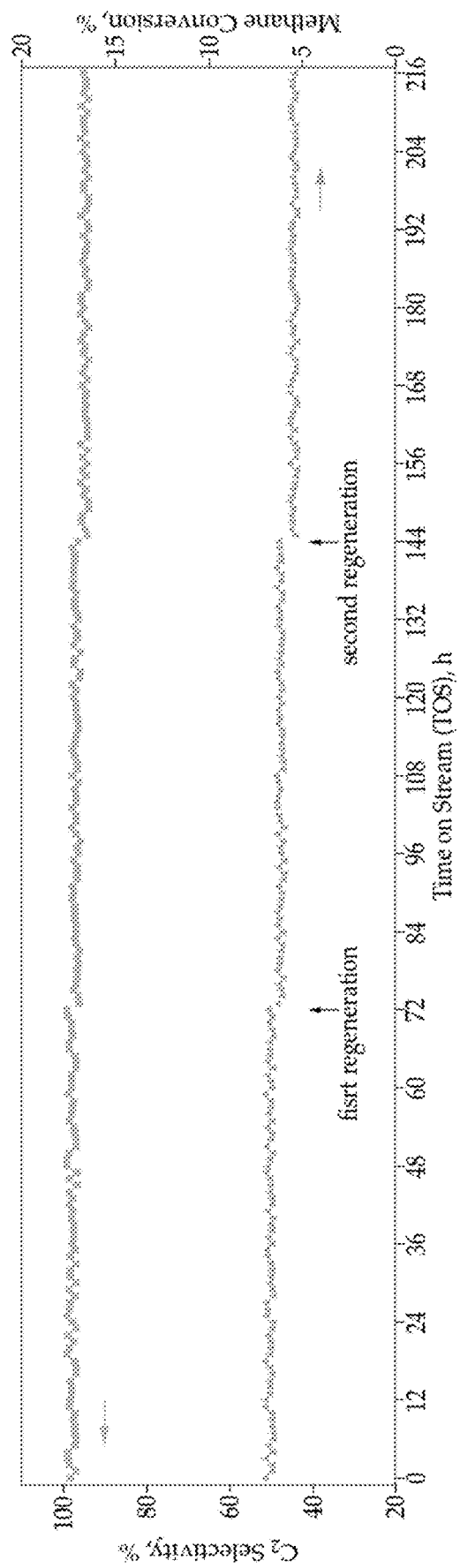
FIG. 13. Long-term catalyst stability and regeneration of 0.5% Pt/MXene at 750° C. and GHSV 8.6 $h^{-1}$.
Figure 14:
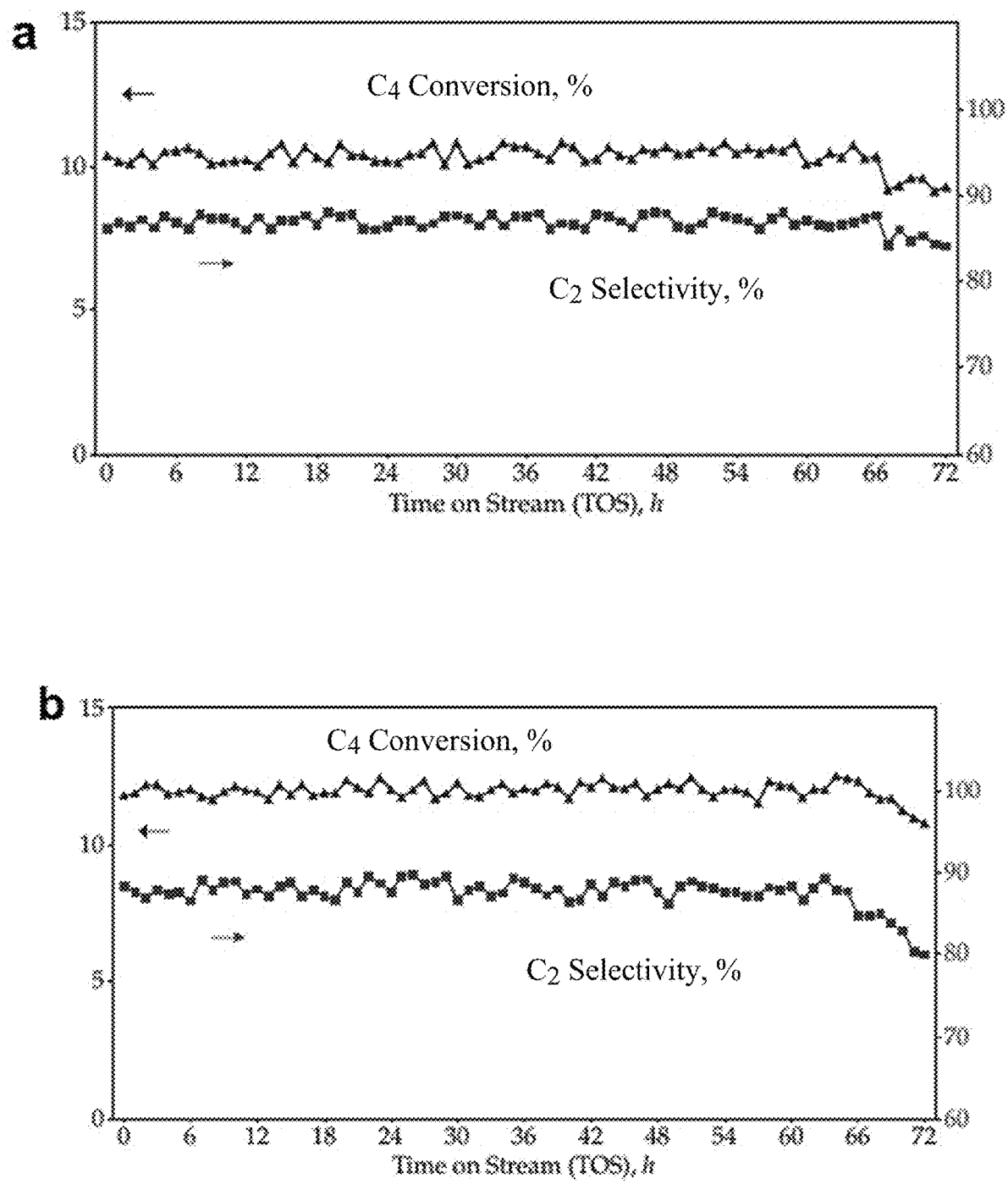
FIG. 14. Long-term catalyst stability of 0.5% Pt/MXene at 800° C. (a) and 850° C. (b) and GHSV 8.6 $h^{-1}$.

Under differential operating conditions (methane conversion <10%) and the absence of mass and heat transfer effects (see Example for details), kinetic measurements were performed for NOCM over 0.5% Pt/Mo$_2$TiC$_2$T$_x$. In the investigated temperature range (700-780° C.), both methane coupling to ethane and ethylene formation from ethane dehydrogenation were first-order reactions (FIG. 12). The activation energies were 205 and 208 kJ/mol (FIG. 3b and Table 4), respectively, consistent with previous literature reports (*Appl. Catal., A,* 2014, 472, 39). In particular, the 0.5% Pt/Mo$_2$TiC$_2$T$_x$ catalyst showed a stable trend without deactivation for 72 hours (3 days) at 750° C. and 8.6 h$^{-1}$ GHSV (FIG. 3c). It should be noted that catalyst regeneration plays a crucial role in the NOCM reaction as coke depositions leading to deactivation of catalysts are considered to be inevitable. We therefore conducted an in situ regeneration treatment by feeding an O$_2$—H$_2$O mixture at 450° C. for 10 hr to test the regenerability of the Pt/Mo$_2$TiC$_2$T$_x$ catalysts. After two cycles of regeneration, the catalyst continued to activate methane to form C$_2$ species with high selectivity (>98%) for an additional six days, although methane conversion decreased slightly by ~1% per regeneration (FIG. 13). At 800 and 850° C., the long-term stability of Pt/Mo$_2$TiC$_2$T$_x$ catalysts was inferior to that of Pt/Mo$_2$TiC$_2$T$_x$ tested at 750° C., showing performance deactivation at time on stream (TOS)=60-65 h (FIG. 14).

TABLE 3

H$_2$—O$_2$ titration results for various Pt/Mo$_2$TiC$_2$T$_x$ catalysts.

| Catalyst | Pt dispersion, % |
|---|---|
| 2.0% Pt | 34 |
| 1.5% Pt | 44 |
| 1.0% Pt | 65 |
| 0.75% Pt | 74 |
| 0.5% Pt | 91 |
| 0.25% Pt | 97 |

TABLE 4

Kinetic Parameters for NOCM.

| | R1 | R2 |
|---|---|---|
| reaction order | 1 | 1 |
| E$_a$, kJ/mol | 205 | 208 |
| A$_i$, 10$^{10}$ kmol/(kg$_{cat}$ · s · atm) | 5.8 | 53.3 |

We further investigated the chemical environment of Pt ADNLs using in situ X-ray absorption spectroscopy (XAS). Comparing 0.5% Pt/Mo$_2$TiC$_2$T$_x$ catalysts reduced at 750° C. with metallic Pt foil, Pt L$_{III}$ edge X-ray absorption near edge spectra (XANES) show that the edge energy increases by 0.3 eV and that the white-line intensity is higher (FIG. 3d), suggesting that the unoccupied 5d states of Pt ADNL shift to higher energy. According to recent literature, the occupied 5d states (valence states) of Pt ADNLs, which are responsible for metal-adsorbate bond energies and catalytic performance, correspondingly shift to lower energy compared to Pt foil (*ChemCatChem,* 2020, 12, 1325). The lower energy of the valence states due to the interactions between ADNLs and Mo$_2$TiC$_2$T$_x$ MXene support results in modified absorptive properties of supported Pt catalysts. FIG. 3e shows the magnitude of the Fourier transform of the k$^2$ weighted extended X-ray absorption fine structure (EXAFS) spectra of the Pt/Mo$_2$TiC$_2$T$_x$ catalysts plotted together with the Pt foil. The first-shell scattering peaks of Pt/Mo$_2$TiC$_2$T$_x$ are in the same distance region (phase-uncorrected distance R=1.5-3.2 Å) as the Pt—Pt scattering peaks from Pt foil, corresponding to metal-metal bonding. The scattering pattern for Pt/Mo$_2$TiC$_2$T$_x$, however, is very different from that of the Pt foil. The peak intensity is greatly reduced at R=2-3 Å (phase uncorrected distances), suggesting strong deconstructive interference on Pt-5d (Pt—Pt) scattering by Pt-4d (Pt—Mo) scattering.

Figure 15:
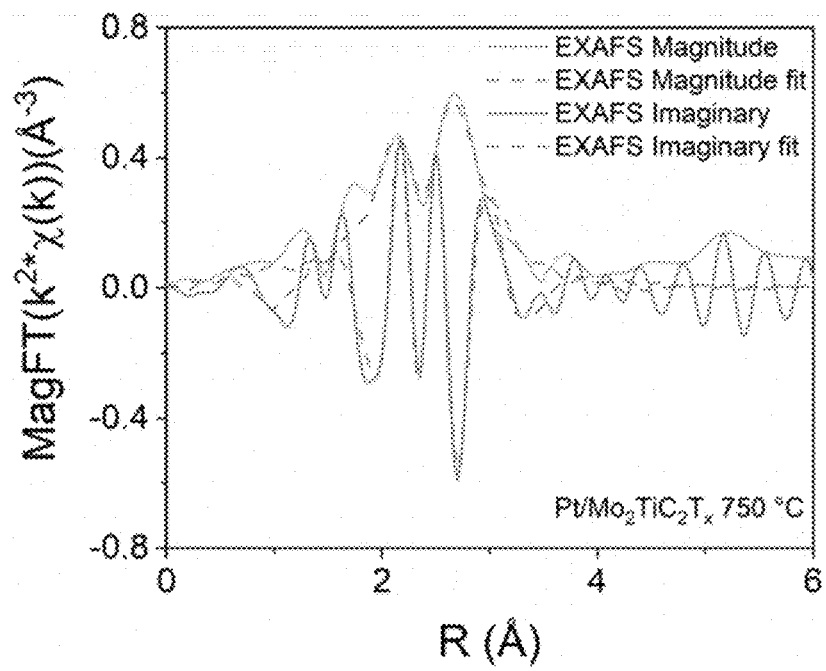
FIG. 15. The magnitude (solid) and imaginary (dash) part of the Fourier transform of the $k^2$ weighted EXAFS and corresponding first shell fit for (a) $Pt/Mo_2TiC_2T_x$-750° C.

Quantitative fitting of the EXAFS spectra gives the following average coordination numbers (CNs) and bond distances for Pt/Mo$_2$TiC$_2$T$_x$ catalysts reduced at 750° C.: 3.2 Pt—Pt bonds at 2.79 Å and 5.8 Pt—Mo bonds at 2.80 Å (FIG. 15). The results suggest that the Pt nanolayers directly bond with the Mo atoms from the MXene support, which is consistent with HAADF-STEM showing that the Pt nanolayers are in direct contact with the Mo atom layers (FIG. 1f). The average Pt—Pt bond distance (2.79 Å) of Pt/Mo$_2$TiC$_2$T$_x$ is slightly longer than that of bulk Pt (2.76 Å), indicating that the strong anchoring of Pt atoms at the C hollow sites is able to overcome the metallic bonding among the Pt atoms. Our DFT calculations (FIG. 16 and FIG. 17) suggest that the first layer of Pt is significantly strained to match the MXene lattice, leading to an expanded lattice distance compared to the second layer of Pt atoms (see Example for discussion).

Figure 18:
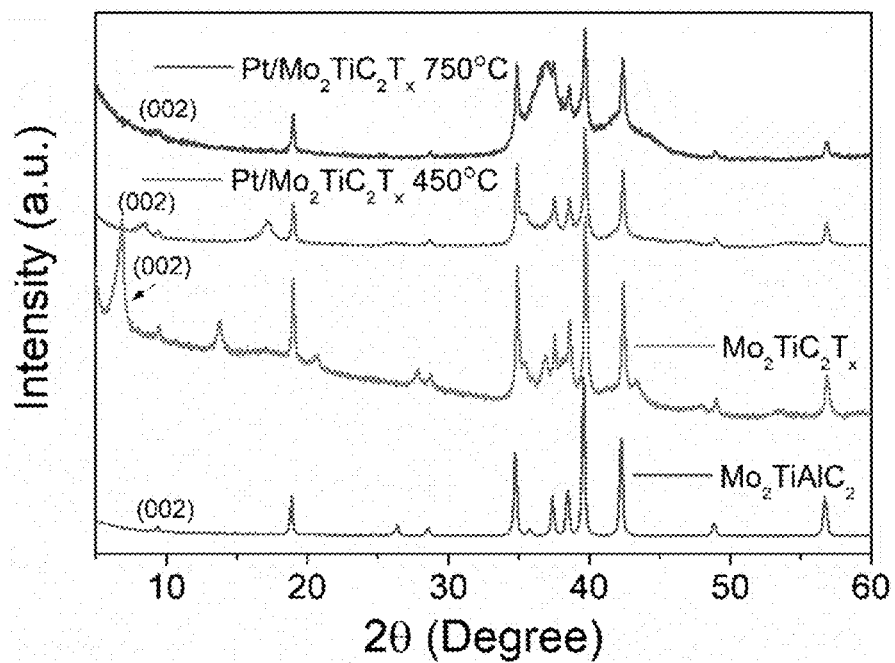
FIG. 18. XRD patterns of $Mo_2TiAlC_2$ MAX, fresh $Mo_2TiC_2T_x$ MXene, $Pt/Mo_2TiC_2T_x$ reduced at 450° C. and $Pt/Mo_2TiC_2T_x$ reduced at 750° C.
Figure 19:
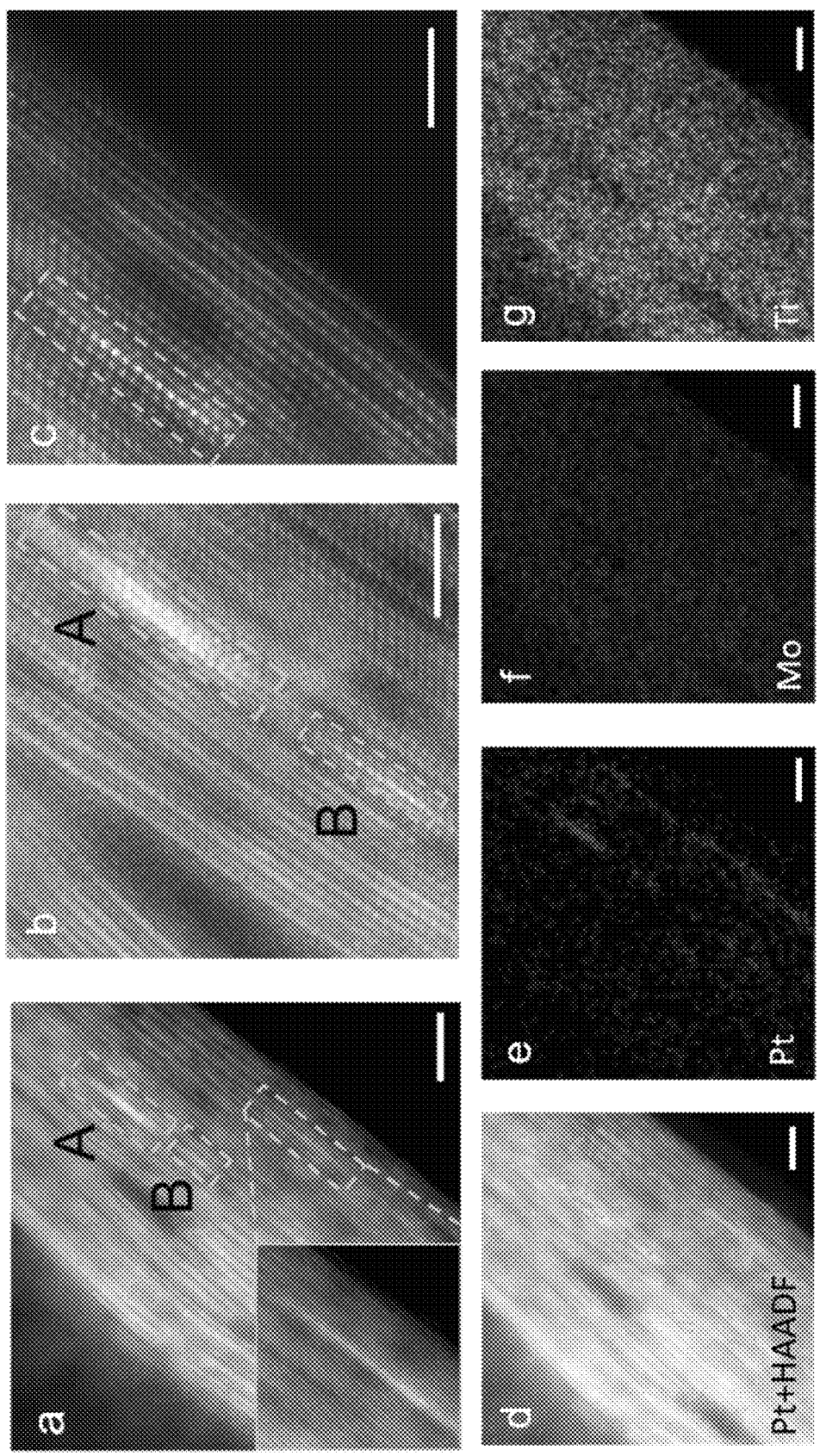
FIG. 19. (a-c) HAADF-STEM image viewing from [11$\bar{2}$0] direction. The Pt monolayers and double layers are marked by orange dash lines and green dash lines, respectively. Scale bar in a-c are 5 nm, 2 nm and 2 nm, respectively. (d-g) STEM elemental mapping of Pt ADNLs supported by $Mo_2TiC_2T_x$ MXene. Scale bar 4 nm.
Figure 20:
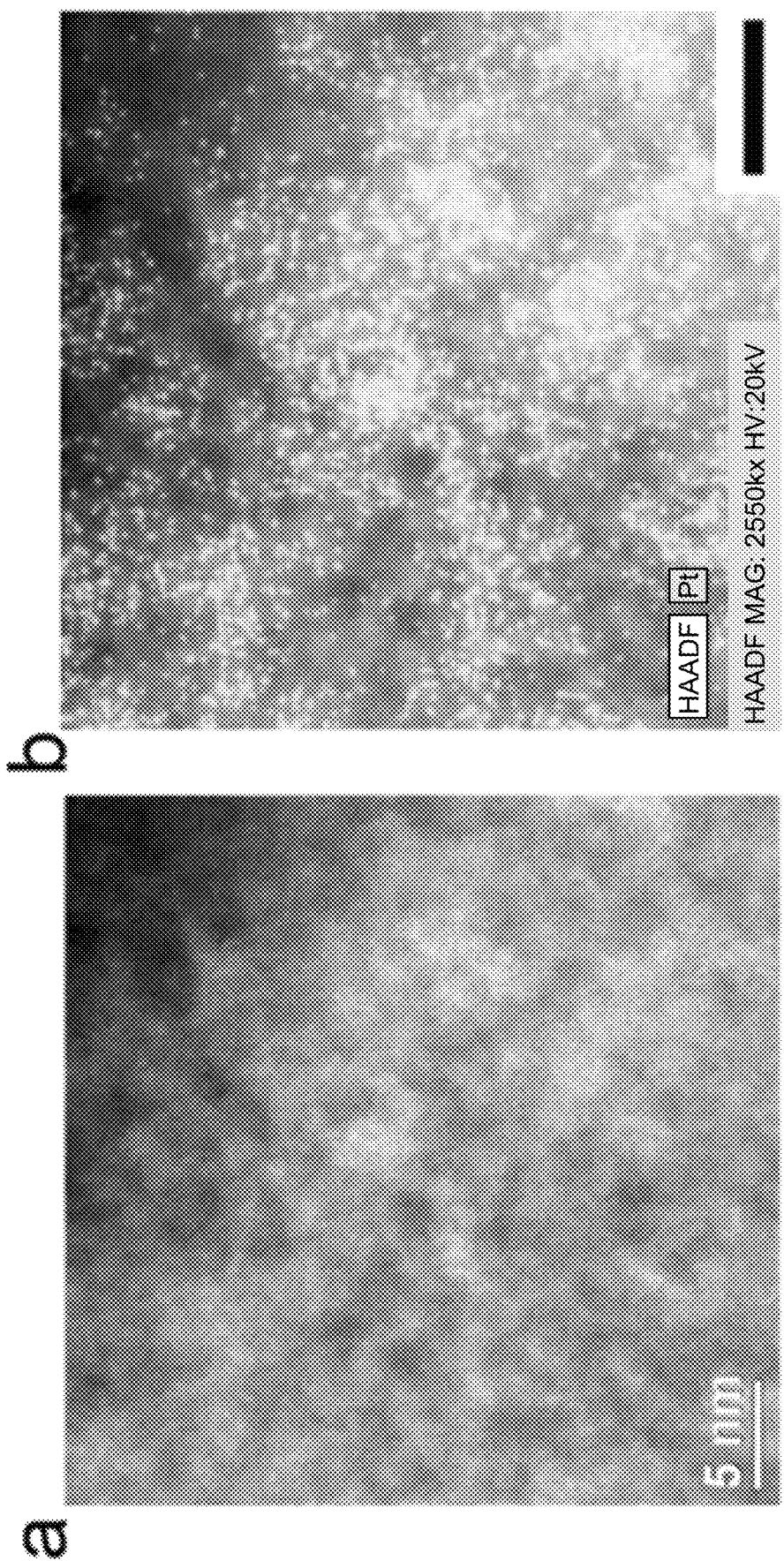
FIG. 20. (a-d) Annular dark-field STEM overview images and EDS elemental mapping of $Pt/Mo_2TiC_2T_x$ reduced at 750° C. Scale bar is 7 nm. EDS analysis is employed to identify the Pt nanolayers easier. (e) Size distribution of more than 100 nanolayers. The average size of the nanolayers is 4.1 nm.
Figure 20:
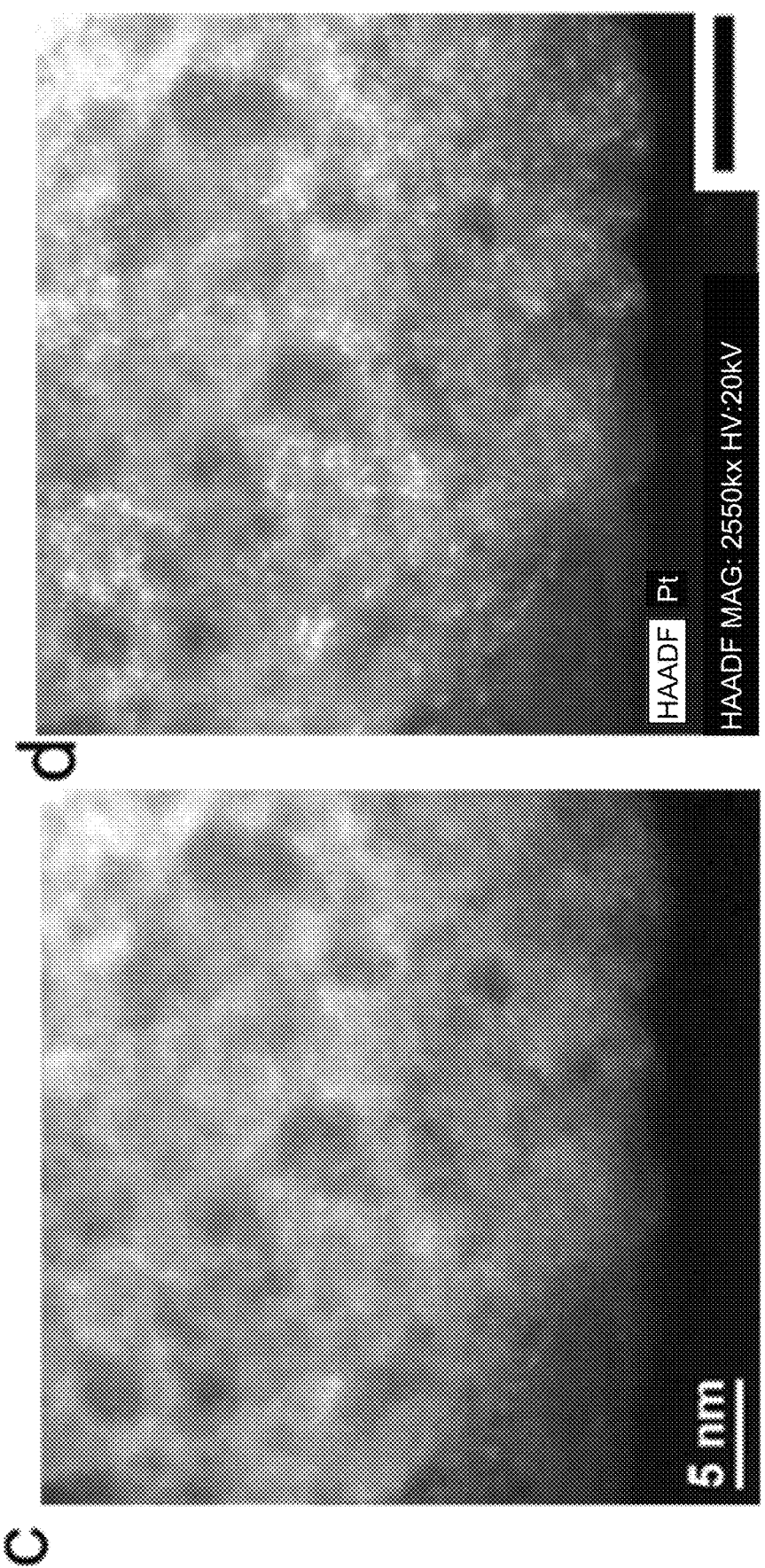
Figure 20:
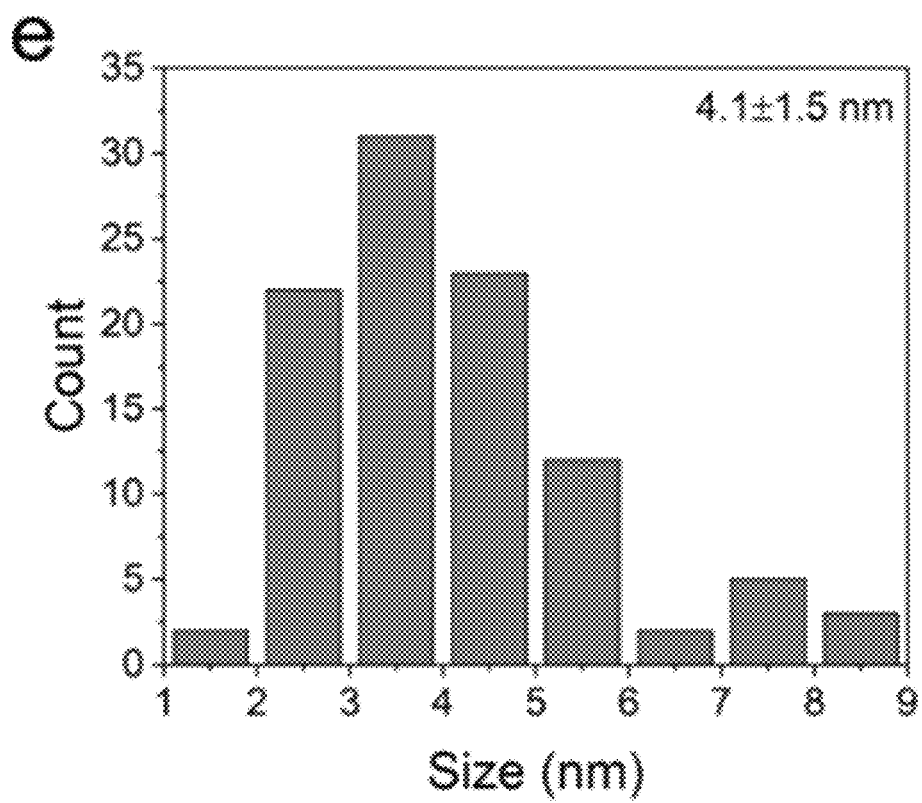

Aberration-corrected HAADF-STEM was executed to examine the structure of 0.5% Pt/Mo$_2$TiC$_2$T$_x$ catalysts reduced at the reaction temperature (750° C.). FIG. 3f and its inset show that the Mo$_2$TiC$_2$T$_x$ support is viewed along the [0001] zone axis, where the hexagonal symmetry is the characteristic structure of Mo$_2$TiC$_2$T$_x$ MXenes and suggests that the support was preserved at the reaction temperature, consistent with the X-ray diffraction (XRD) results (FIG. 18). An image at higher magnification (FIG. 3g) and corresponding EDS elemental mapping (FIG. 3h) confirm the continuous lattice fringes of the Pt ADNLs on the Mo$_2$TiC$_2$T$_x$ MXene support, indicating that epitaxial growth of Pt on MXenes was retained under high temperature reduction. HAADF-STEM images viewed along the [11$\bar{2}$0] zone axis display that single or double atomic layers of Pt intercalated between layers of the MXene support (FIG. 19), consistent with Pt/Mo$_2$TiC$_2$T$_x$ catalysts reduced at the activation temperature (450° C.). The EDS element mappings show that ADNLs of Pt with an average diameter of approximately 4.1 nm (FIG. 20) are on the surfaces of MXene supports and that no agglomerated nanoparticles were formed at the reaction temperature. Together, HAADF-STEM and EXAFS indicate that Pt metal-support bonding anchors Pt ADNLs on the surface of MXene supports, which renders Pt/Mo$_2$TiC$_2$T$_x$ highly stable and sintering-resistant catalysts for NOCM at 750° C.

Figure 4:
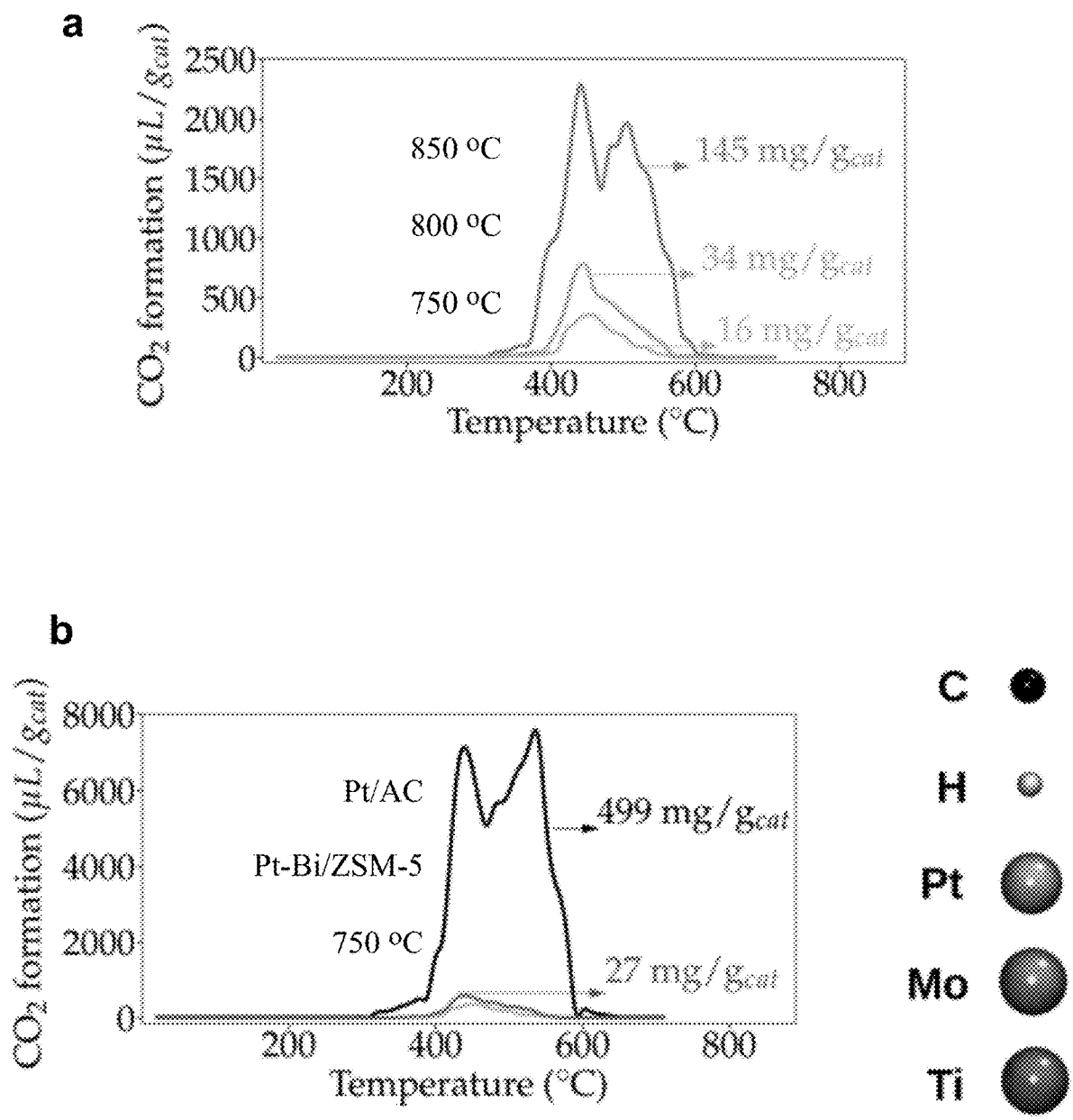
FIG. 4. Oxidation tests and DFT calculations. a,b, TPO profiles for spent 0.5% $Pt/Mo_2TiC_2T_x$ catalyst at GHSV 8.6 $h^{-1}$ at 850° C., 800° C. and 750° C. after 72-h tests (a); Pt—Bi/ZSM-5 and Pt/AC (activated carbon) (b). c, Energy landscape and DFT optimized configurations for NOCM on a single Pt nanolayer (111) (blue), dual Pt nanolayer (111) (green), and Pt nanoparticle (111) (red).
Figure 4:
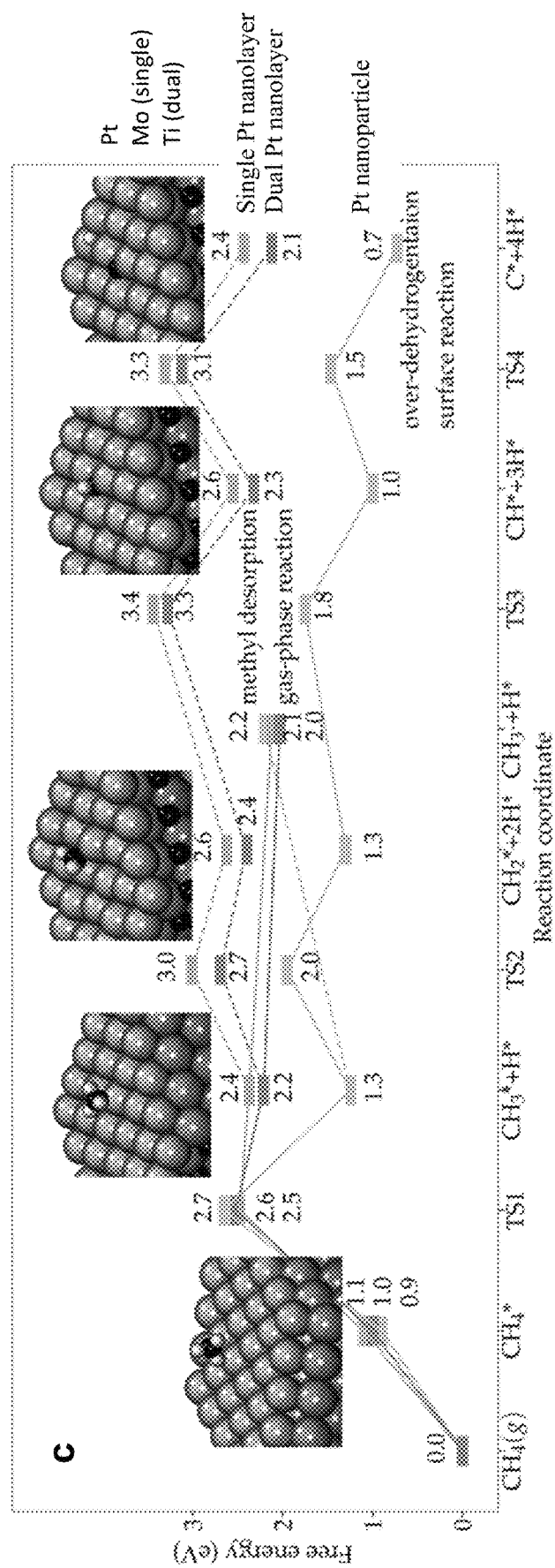
Figure 21:
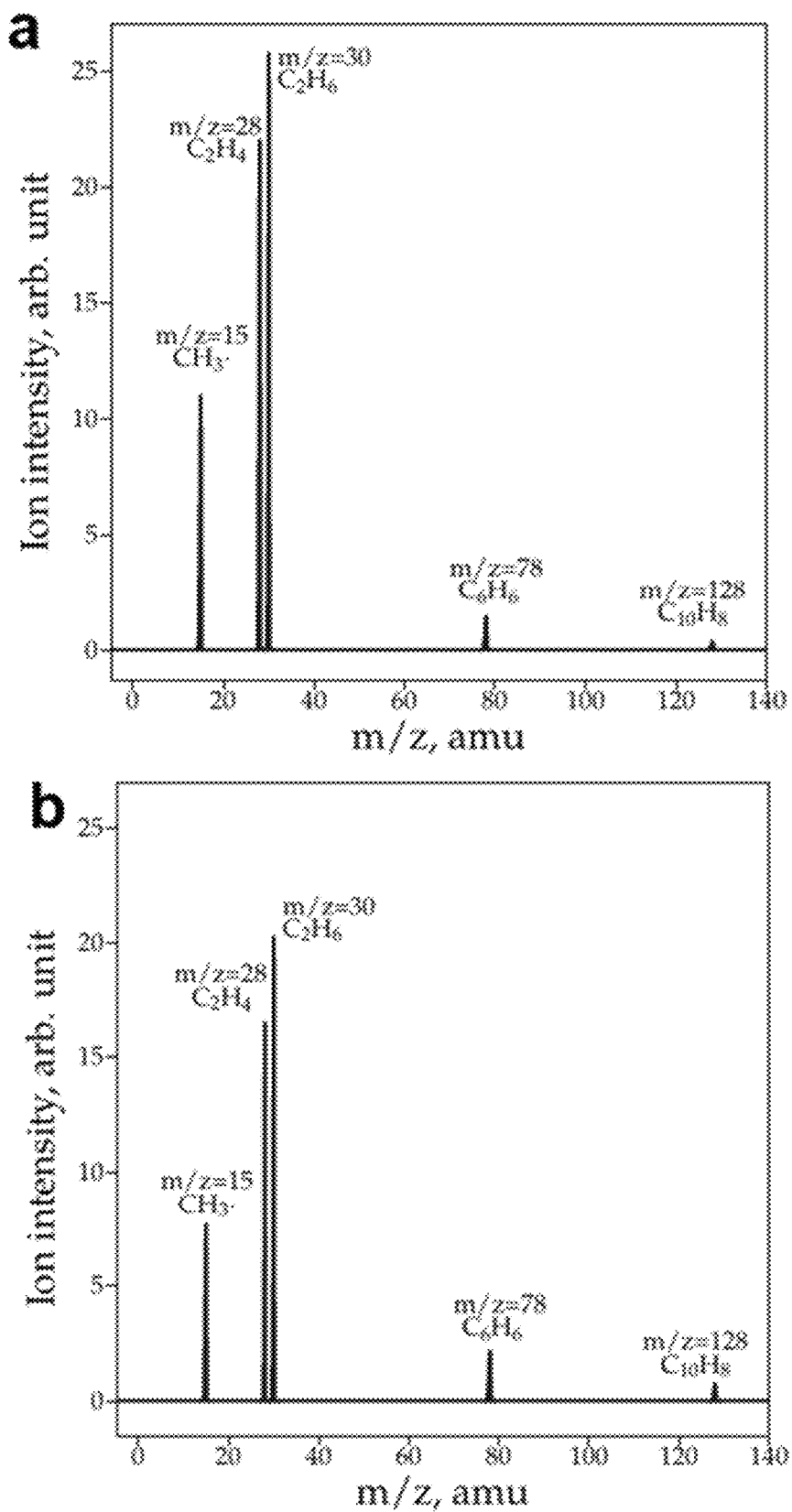
FIG. 21. The full mass spectra of reactor outlet over 0.5% Pt/MXene at 750° C. (a), 800° C. (b) and 850° C. (c) in GHSV (gas hourly space velocity) for 72 hours range 8.6 $h^{-1}$.
Figure 21:
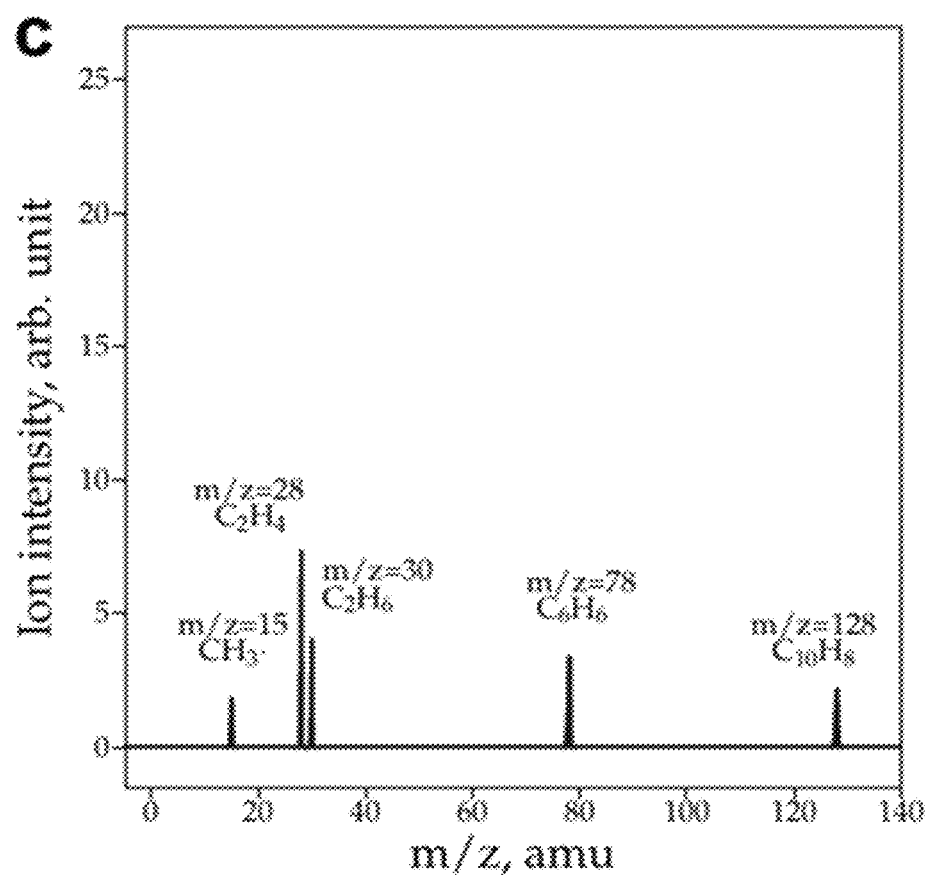

We employed temperature-programmed oxidation (TPO) to investigate the coke formation of spent 0.5% Pt/Mo$_2$TiC$_2$T$_x$ catalysts tested at various temperatures and to compare them with Pt or bimetallic nanoparticle catalysts. The TPO profile of spent Pt/Mo$_2$TiC$_2$T$_x$ catalysts tested at 750° C. after 72 hours shows a major peak near 450° C. (FIG. 4a). With the increase in the reaction temperature, a broad shoulder on the high-temperature side starts to evolve and develops into a distinguishable peak at 510° C. for catalysts tested at 850° C., corresponding to at least two different types of carbon species. Moreover, our mass spectra results demonstrate that the concentrations of ethane, ethylene and methyl radicals started to decrease when the reaction temperature was higher than 800° C., while the peaks of benzene (m/z=78) and naphthalene (m/z=128), as coke precursors, increased, especially at 850° C. (FIG. 21). This observation implies that high operating temperatures (>800° C.) led to heavier aromatics as coke precursor species that resulted in the deactivation of the catalysts.

Figure 22:
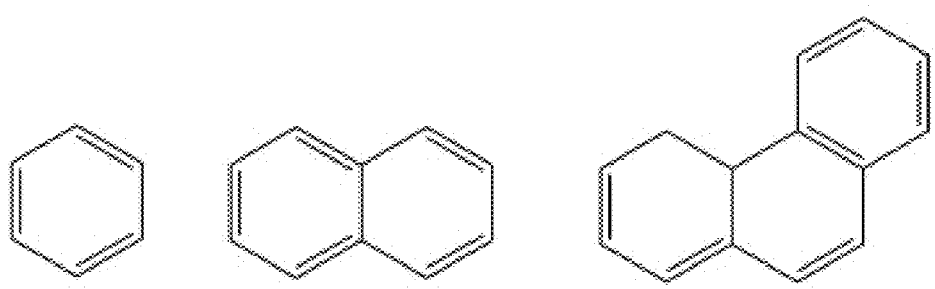
FIG. 22. Coke compounds detected by GC-MS.
Figure 22:
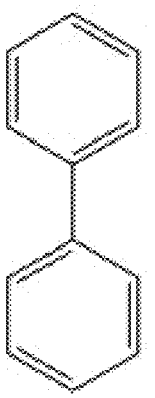
Figure 22:
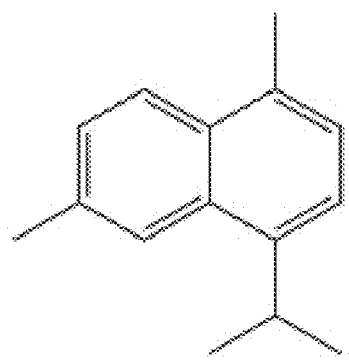
Figure 22:
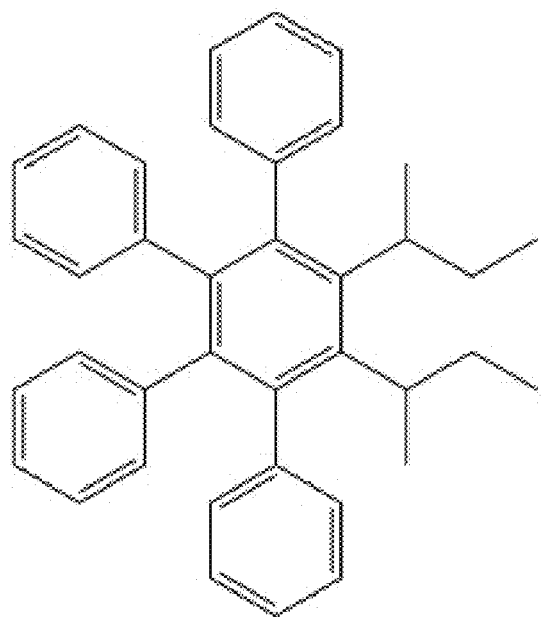
Figure 23:
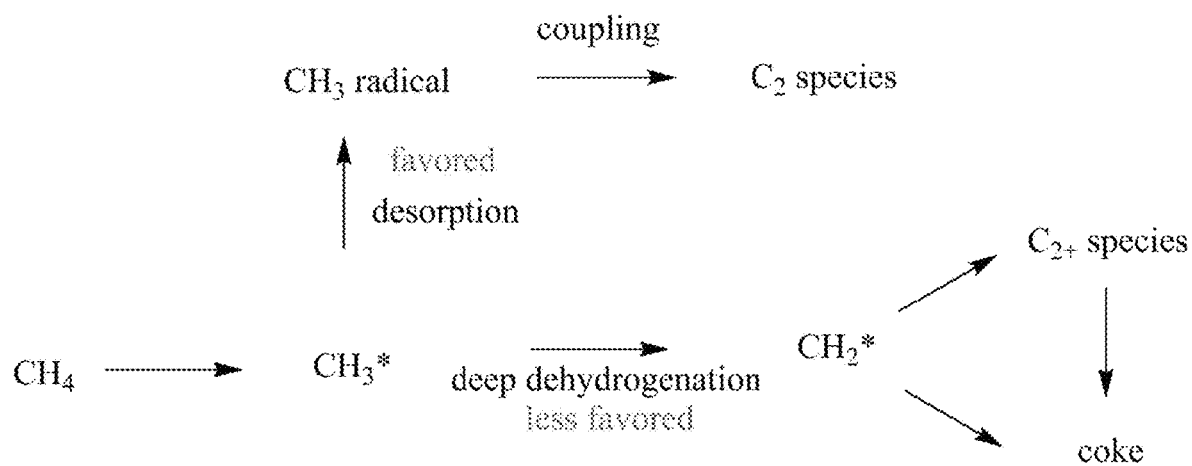
FIG. 23. Scheme of the hydrocarbon pool NOCM mechanism for $Pt/Mo_2TiC_2T_x$.

The coke residues of Pt/Mo$_2$TiC$_2$T$_x$ catalysts after the TPO tests were dissolved in a mixture of ethanol and acetone and were analyzed by GC-MS; in addition to benzene and naphthalene, C$_{12}$-C$_{38}$ polyaromatic hydrocarbons were the primary coke-representing compounds (FIG. 22). Coke formation of NOCM is proposed via the well-known hydrocarbon pool mechanism, which was originally proposed for MTO (methanol to olefins) but has also been applied to methane nonoxidative conversion. In general, it was hypothesized that the CH$_2$* component, formed by the over-dehydrogenation of CH$_3$*, serves as the core species in the hydrocarbon pool (FIG. 23), which can be converted to heavier hydrocarbons such as C$_3$-C$_6$, C$_6$+, and eventually coke. Deep dehydrogenation of CH$_3$* is favored at high operating temperatures, leading to CH$_y$* (y≤2) that serve as coke precursors. It should be noted that Pt/Mo$_2$TiC$_2$T$_x$ operated at 750° C. exhibited the lowest amount of coking compared with Pt nanoparticles supported by activated carbon and Pt—Bi bimetallic nanoparticles on ZSM-5 zeolites (FIG. 4b), which results in the long-term stability of the catalysts at the optimal reaction temperature (750° C.).

DFT studies. To gain more insights into the suppressed coke deposition of the ADNL catalysts for the NOCM reaction, the energy profiles of the NOCM reaction and possible side reactions were studied by DFT calculations. Snapshots of the structures of reaction intermediates and transition states are illustrated in FIG. 4c, with the free energies of the relevant reaction pathways on Pt nanoparticle (111) surfaces and ADNLs calculated. NOCM starts with the activation of the first C—H bond that leads to dissociative adsorption of methane forming surface alkyl species (CH$_3$*). Our DFT results suggest that the free energy changes of all C—H bond scission steps on the Pt monolayers and double nanolayers are ~1 eV more unfavorable than those on Pt nanoparticles (111), indicating significantly weakened surface adsorption activity of the ADNLs due to the altered electronic structure suggested by XANES. Such a weakening leads to the preferential desorption of surface alkyl species to form methyl radicals instead of the scission of the remaining C—H bonds towards deep dehydrogenation, which is believed to generate precursors leading to coke deposition.

On ADNLs at 750° C., the scission of a secondary C—H, i.e., from CH$_3$* to CH$_2$*, is endergonic (0.2 eV), while CH$_3$* desorption is exergonic (ca. −0.2 eV). Furthermore, compared with the energy barrier associated with conversion of CH$_3$* to CH$_2$* (TS2), CH$_3$* desorption to methyl radicals is even more preferred, with an energy difference of approximately 0.7-0.9 eV. This is primarily due to the relatively weak adsorption of CH$_3$* over ADNLs. In contrast, the deep dehydrogenation step is more favored over the (111) surface of Pt nanoparticles, by approximately 0.2-0.3 eV in free energy, indicating that the formation of a methyl radical is less favorable than further dehydrogenation. Compared to the methyl desorption step, C—H bond scissions of over-dehydrogenated reaction intermediates, e.g., CH$_2$* and CH*, are both exergonic and much more favorable. These findings rationalize our experimental observations that Pt/Mo$_2$TiC$_2$T$_x$ catalysts readily activate C—H bonds in methane to form CH$_3$*, which is prone to desorption from the surface of ADNLs instead of over-dehydrogenation, leading to higher selectivity to C$_2$ products while resisting coke formation.

Figure 24:
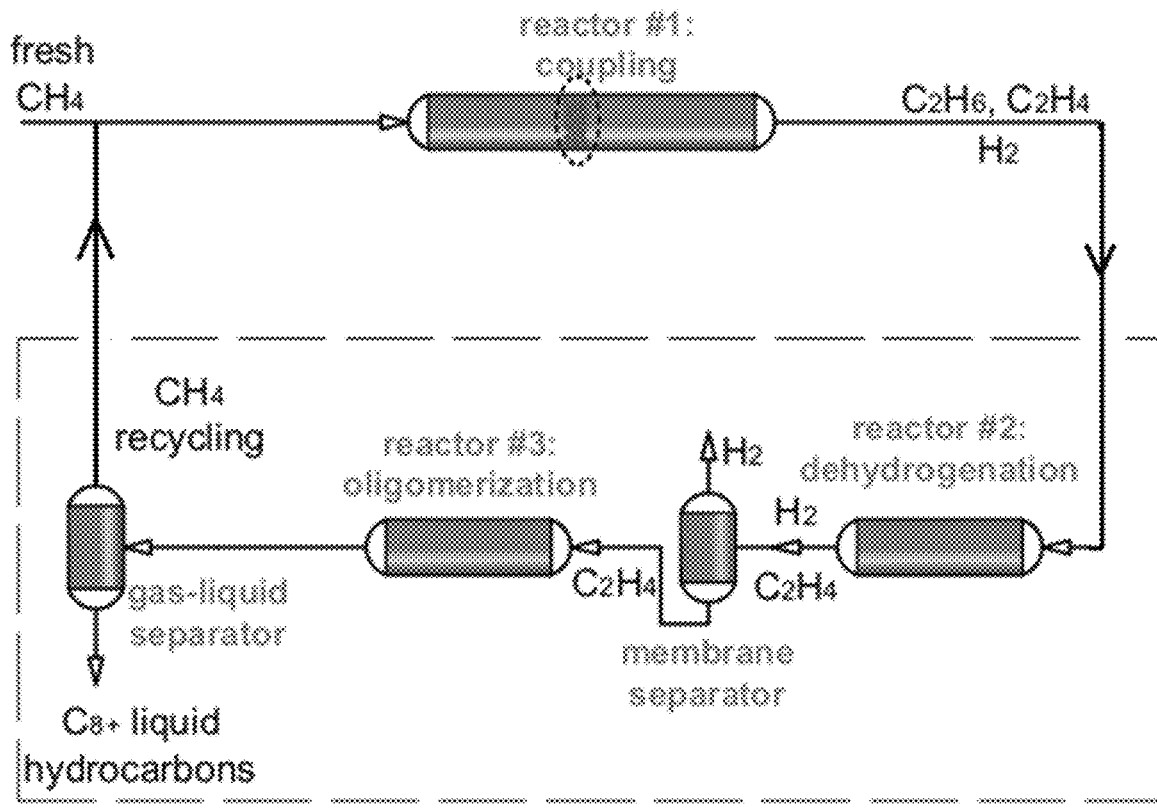
FIG. 24. A proposed flow diagram for converting methane to $C_{8+}$ liquid hydrocarbons. The process includes three chemical reactors and two separators: reactor 1 is for nonoxidative coupling of methane (NOCM) to ethane/ethylene, and reactor #2 dehydrogenates the ethane to ethylene. After hydrogen is removed by a membrane separator, ethylene is converted to $C_{8+}$ liquid hydrocarbons via oligomerization in reactor #3. Then the target liquid hydrocarbons can be separated from unreacted methane in a gas-liquid separator.

In summary, our experimental and theoretical results demonstrated the epitaxial growth of atomically dispersed Pt nanolayers on the surface of Mo$_2$TiC$_2$T$_x$ MXene. We found that ADNLs of Pt were anchored on the MXene through strong Pt—Mo bonding at the metal-support interfaces, which leads to atomic dispersion and altered absorptive properties of the Pt active sites that favor methane coupling over coking formation. Consequently, Pt/Mo$_2$TiC$_2$T$_x$ catalysts delivered stable methane conversion to C$_2$ products with >98% selectivity and TOFs of 0.2-0.6 s$^{-1}$, which are approximately 1,000-times higher than those of the Pt-based bimetallic nanoparticle catalysts reported in the literature at similar temperatures. The catalysts are available for regeneration, leading to long-term (9 days) stability that is favored by practical applications and catalyst commercialization. Since commercial processes have been developed for converting C$_2$ (ethane/ethylene) to liquid hydrocarbon (C$_{8+}$) (FIG. 24), the NOCM is the last part remaining unsolved, which merits future research attention for visible industrial methane-to-liquid technology.

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLE

Example 1. Materials and Methods

Synthesis of Mo$_2$TiAlC$_2$ and Mo$_2$TiC$_2$T MXene. A spark plasma sintering (SPS) was employed to synthesize Mo$_2$TiAlC$_2$ (MAX phase). In detail, commercial powders of molybdenum (Sigma Aldrich, 99%), titanium (Alfa Aesar, 325 mesh, 99%), aluminum (Alfa Aesar, 325 meshes, 99.5%) and graphite (Alfa Aesar, 7-11 micron, 99%) were mixed in a molar ratio of Mo/Ti/Al/C=2:1:1.1/1.9. The mixture was transferred into a graphite die coated with boron nitride. We added excess Al and less than a full equivalent of graphite because a small portion of Al will vaporize during high-temperature sintering, and carbon deficiencies exist in most Al-containing MAX phases. Then, the graphite die was loaded in a Fuji-21 1lx SPS system and sintered at 1450° C. under 30 MPa for one hour. The synthesized Mo$_2$TiAlC$_2$ disk was then pulverized and sieved through a 400-mesh screen. The Mo$_2$TiAlC$_2$ powder was treated with 48% HF at 55° C. for 72 hours. The resulting Mo$_2$TiC$_2$T$_x$ MXene was then washed with deionized (DI) water until the pH reached ~5. The MXene powder was collected by centrifugation at 8900 rpm and then dried under vacuum at ambient temperature.

Synthesis of Pt/Mo$_2$TiC$_2$T$_x$. For a typical synthesis, 0.20 g of Pt(NH$_3$)$_4$(NO$_3$)$_2$(Sigma Aldrich, 99.995%) was dissolved in 1 mL of deionized water (DI) $H_2O$ to prepare 0.02 g Pt/mL. Pt was loaded on $Mo_2TiC_2T_x$ supports via incipient-wetness impregnation (IWI). Different Pt loadings were achieved by varying the volume of Pt solution used. After the impregnation of Pt, the materials were dried overnight under vacuum at room temperature. Fresh $Pt/Mo_2TiC_2T_x$ was directly used for kinetics tests and other treatments. For reduced $Pt/Mo_2TiC_2T_x$, the fresh $Pt/Mo_2TiC_2T_x$ powder was transferred into a tube furnace and reduced at different temperatures for at least 30 min under a 3% $H_2$/Ar flow with a ramping rate of 5° C./min.

Composition and structure characterization. The mass loading of Pt was determined by using a Thermo Fisher Scientific X Series 2 inductively coupled plasma mass spectrometer (ICP-MS). All Pt-containing samples were digested in a boiling aqua regia solution, and the clear top layers were used for further analysis. X-ray diffraction (XRD) patterns were recorded at room temperature by a 4 Bruker diffractometer with a Cu Kα radiation source ($\lambda$=1.5406 Å). High-resolution, high-angle annular dark-field (HAADF) scanning transmission electron microscopy (STEM) imaging was acquired on a Titan Themis 300 probe corrected TEM with a Super-X EDX detector in the Sensitive Instrument Facility of Ames Lab.

We conducted X-ray absorption measurements at the Pt $L_{III}$ edge (11.5640 keV) on the bending magnet beam line of the Materials Research Collaborative Access Team (MR-CAT) at Sector 10 in the Advanced Photon Source, Argonne National Laboratory. Samples for fluorescence were ground into a fine powder and pressed into a stainless-steel sample holder with the catalyst wafer oriented 45 degrees relative to the X-ray beam. The cell used for fluorescence measurement consisted of a water-cooled stage fitted with Kapton windows for fluorescence and transmission measurements. For treatments, the cell was equipped with water cooling and ceramic heaters for temperature control and valves for gas flow. The $Pt/Mo_2TiC_2T_x$ catalyst was heated to 750° C. in 3.5% $H_2$ for 30 minutes and cooled to 200° C. in 3.5% $H_2$ for analysis. Fluorescence was measured using a standard 3.3 cm Lytle detector with a Pt foil used to reduce background fluorescence. Fluorescence X-rays diffract through the logarithmically bent crystal and are angularly dispersed downstream of the crystal. By choosing the correct detector angle relative to the bent crystal, the Pt Lα fluorescence line was selectively collected. Athena was used for energy calibration, background subtraction and normalization of XAS data. The EXAFS data were fitted by Artemis to determine the coordination number (CN), bond distance (R), energy shift ($\Delta E_o$) and Debye Waller factor ($\Delta\sigma^2$). The k range for the Fourier transform of the Pt K edge was $\Delta k$=3~11 Å$^{-1}$, and the R range for fitting was $\Delta R$=1.5~3.2 Å. The amplitude reduction factor ($S_0^2$=0.80) was determined by the standard Pt foil, and CN, bond distances and Debye-Waller factor were adjusted from an initial structural model until a good fit was obtained.

By $N_2$ adsorption and desorption at 77 K via a Micromeritics ASAP 2020 apparatus, BET measurements were conducted, giving physisorption properties of catalysts, including surface area, pore size and pore volume. Before measurements, degassing was carried out at 300° C. for 8 hrs. Elemental analysis of catalysts was carried out by the ICP-AES method (SPECTRO Instrument). For Pt-loaded catalysts over MXenes, $H_2$—$O_2$ titration was carried out at room temperature to measure Pt dispersion.

Kinetics measurements and analysis. The catalytic performance tests and kinetics measurements were conducted in a fixed-bed reactor Prior to testing, activation of the packed catalyst was performed at 450° C. for 4 hours under a $H_2$—$N_2$ mixture flow ($H_2$: $N_2$=1:2, 100 std cc/min). The reactor was then purged by nitrogen with a flow of 50 std cc/min for 15 min.

Various GHSV (gas hourly space velocity) values were achieved by varying the packed amount of catalysts and feed flow rates. The standard operating conditions were 750° C., 0.01 atm methane partial pressure, and 50 mg of catalyst. The absence of mass transfer limitations, including both internal and external diffusion, was also confirmed by satisfying the Weisz and Prater criterion (*Adv. Catal.*, 1954, 6, 60390), while the Mears criterion was used to exclude heat transfer effects (*Phys. Rev. B*, 1996, 54, 11169).

A GC (Agilent GC6890) with both flame ionization detector (FID) and Thermal conductivity detector (TCD), equipped with a Carboxen 1010 PLOT capillary column (30 m×0.53 mm) was used for quantitative analysis of products. In typical cases, following an initial transient period, the catalyst exhibited stable performance for several hours. Unless stated otherwise, all data sets were taken at 10 min time on stream (TOS) during the stable period. A blank test of the MXene support with no Pt loading was carried out under standard operating conditions, with the methane conversion always less than 0.01%. All experiments have carbon mass balances of 98.8±0.9%. For the reaction experiments, good repeatability generally within less than 1.5% deviation was achieved for all quantitative analyses. For TPSR experiments, the catalyst was reduced using 5 vol % $H_2$ at 400° C. for 2 hours before the TPSR measurement. Upon cooling to room temperature, a 5% $CH_4$ in $N_2$ gas mixture flow was fed at 20 mL/min, and the temperature was increased from room temperature to 900° C. at a heating rate of 5° C./min. A TCD was used to detect products. In the TPO process, 5% $O_2$ in a $N_2$ gas mixture was used as the oxidizing gas. The used catalysts were packed in the reactor for TPO. For catalyst regeneration, a 5% steam and 5% $O_2$ mixture is prepared and fed into the reactor where the spent catalyst is packed. Then, the reactor was heated to 450° C. and maintained constant for 10 hours. When regeneration was accomplished, the gas was switched to $N_2$ for purging for 15 min, followed by feeding 20% $H_2$ at 450° C. for catalyst activation before use.

The equilibrium methane conversion was calculated based on the standard Gibbs formation energy of chemical species, provided by the NIST JANAF database (http://kinetics.nist.gov/janaf/) and the Aspen plus 8.8 software package. We consider a series reaction as below:

$$CH_4 \xrightarrow{r_1} C_2H_6 \xrightarrow{r_2} C_2H_4 \qquad (1)$$

In the investigated temperature range (700-780° C.), both reactions are determined to be first-order reactions (FIG. 12). The reaction rates can be expressed by the power rate law given below:

$$-\frac{dF_{CH_4}}{dW} = -r_1 = k_1 \times P_{CH_4} \qquad (2)$$

$$\frac{dF_{C_2H_6}}{dW} = r_1 - r_2 = k_1 \times P_{CH_4} - k_2 P_{C_2H_6} \qquad (3)$$

$$\frac{dF_{C_2H_4}}{dW} = r_2 = k_2 \times P_{C_2H_6} \qquad (4)$$

The reaction rates of methane coupling to ethane ($r_1$) and ethane dehydrogenation to ethylene ($r_2$) are described by Equations (2-4), in which only two equations are independent. Based on Equation (2) and Equation (4), $r_1$ is a function of methane partial pressure ($P_{CH_4}$), while $r_2$ is a function of ethane partial pressure ($P_{C_2H_6}$). F is the mole flow rate, and W is the weight of catalysts packed in the flow reactor.

DFT computational methods. Density functional theory (DFT) calculations were performed on the MXene-Pt system using the Vienna Ab initio Simulation Package (VASP). Electron wavefunctions were solved using the projector augmented wavefunction (PAW) method with a plane wave basis set cutoff of 520 eV. The Perdew-Burke-Ernzerhof (PBE) parameterization of the generalized gradient approximation (GGA) was used to calculate the electron exchange and correlation. The energy convergence criteria for all self-consistent field calculations was set as $10^{-5}$ eV, and all structural relaxations were performed until forces were less than 0.02 eV/Å. The DFT-D3 method of Grimme (*J. Chem. Phys.*, 2010, 132, 154104) was applied to account for the van der Waals interactions between atoms. For structural optimization of a single unit cell of the MXene monolayer, a 12×12×1 gamma centered k-point mesh was used. For larger unit cells consisting of 8×8 unit cells of the MXene monolayer and Pt film or nanoparticles, we used a 2×2×1 k-point mesh in our calculations. A vacuum separation of more than 20 Å was kept on top of the MXene layer to prevent interaction with its periodic image. The climbing-image nudged elastic band method was used to locate the structures of transition states (TS) in the reactions. Each transition state was confirmed to have only one imaginary vibrational mode by vibrational normal mode analysis. All free energies were ZPE-corrected, and the change in entropies for adsorption processes was calculated using the operating reaction temperature and the relationship proposed by Campbell (*Z. Phys. Chem.*, 2013, 227).

DFT calculations of methane coupling reaction on Pt ADNLs and nanoparticles. The periodic plane-wave-based code VASP was used for all the DFT calculations, employing the projector augmented wave method for ionic cores and the PW91 form of exchange-correlation functional in the generalized-gradient approximation. The plane-wave cutoff energy level for all calculations was set as 400 eV, while a first-order Methfessel-Paxton smearing with a width of 0.15 eV was evaluated by extrapolating to zero broadening. Monkhorst Pack meshes of 7×7×1 k points were used to sample the surface Brillouin zone for p(2×2) unit cells of Pt (111) and $Mo_2TiC_2T_x$ slabs. A Pt layer was inserted into two $Mo_2TiC_2T_x$ layers to represent our Pt/$Mo_2TiC_2T_x$ catalyst. The reaction of methane activation occurs at the surface of Pt (111) and Pt/$Mo_2TiC_2T_x$, representing Pt nanoparticles and Pt nano-layers, respectively. The free energy of the adsorbed state was calculated based on the adsorption energy, in which the corrections of ZPE and entropy effect were included.

To understand the reason for preferential stability of platinum nanolayers on $Mo_2TiC_2T_x$ MXene substrates instead of nanoparticles, we perform density functional theory (DFT) calculations of the MXene-Pt system. The details of the calculation parameters can be found in the methods section. Initially, structural relaxation of $Mo_2TiC_2T_x$ MXene monolayer is performed. The optimized in-plane lattice constants are a=b=2.94 Å with a Mo—C bond length of 2.08 Å and a Ti—C bond length of 2.15 Å, which are in good agreement with previous DFT calculations of this material and our HAADF-STEM results. The Pt atoms can be situated at either of the three hollow sites on top of Mo, C and Ti, as shown in FIG. 8. To compare the stability of Pt at the different sites, the interface formation energy on the basis of per adsorbed Pt atom is calculated as:

$$E_{IFE} = (E_{MXene+Pt} - E_{MXene} - n * E_{Pt,bulk})/n$$

Here, $E_{MXene+Pt}$, $E_{MXene}$, and $E_{Pt,bulk}$ are the DFT calculated lattice energies of the combined system, MXene substrate and bulk Pt lattice (on a per-Pt-atom basis), respectively, and n is the number of adsorbed Pt atoms. We chose the reference to be the bulk Pt instead of the respective nanostructures, facilitating a uniform and fair comparison across the different nanostructure geometries later. By varying the positions of the Pt atoms and comparing the interface formation energies of systems, we found that the hollow site above C is the most favorable sites for Pt atoms compared to the other two cases (FIG. 8). Subsequently, structural relaxation calculations are carried out on an approximately 1 nm×1 nm Pt monolayer supported by the MXene support. Two geometries of nanoparticles are also studied, each of which contains the same number of Pt atoms as the Pt nanolayer (FIG. 1*j*). The preferential stability of the different nanostructures is once again compared using the interface formation energy as defined above. The Pt nanolayers are oriented with (111) planes of the fcc lattice parallel to (0001) planes of $Mo_2TiC_2T_x$ MXene supports that are in hcp symmetry.

Figure 16:
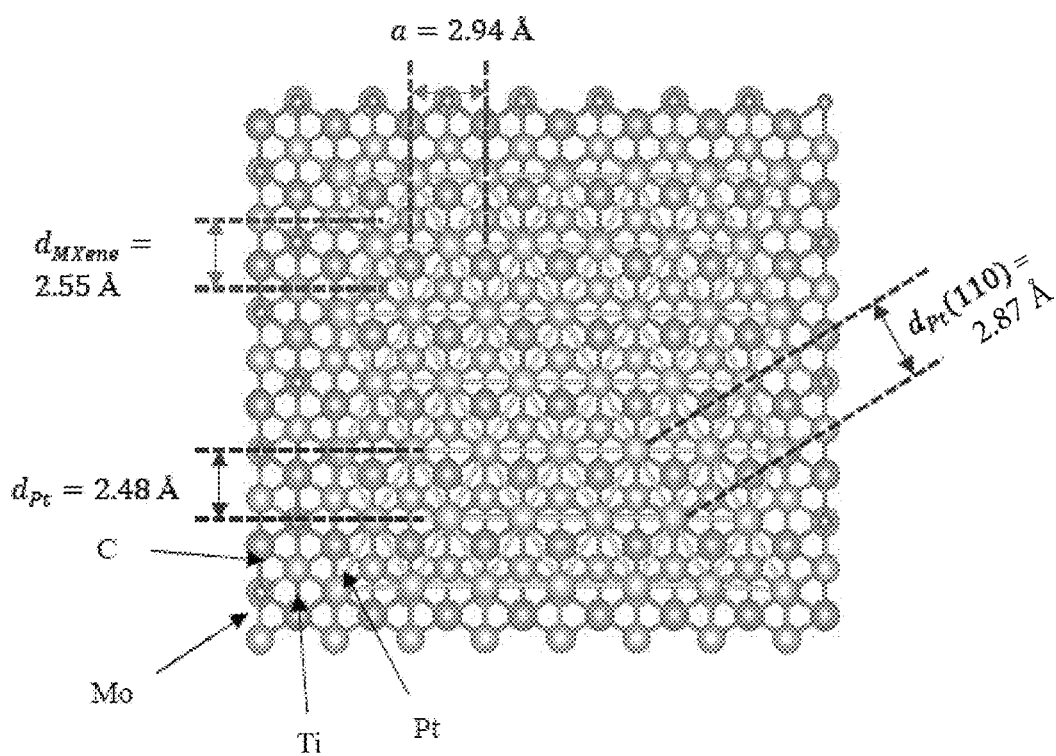
FIG. 16. Relaxed structure of single atomic layer thick Pt monolayer on top of $Mo_2TiC_2T_x$ MXene substrate. Pt (red), Mo (blue), Ti (green) and C (black).
Figure 17:
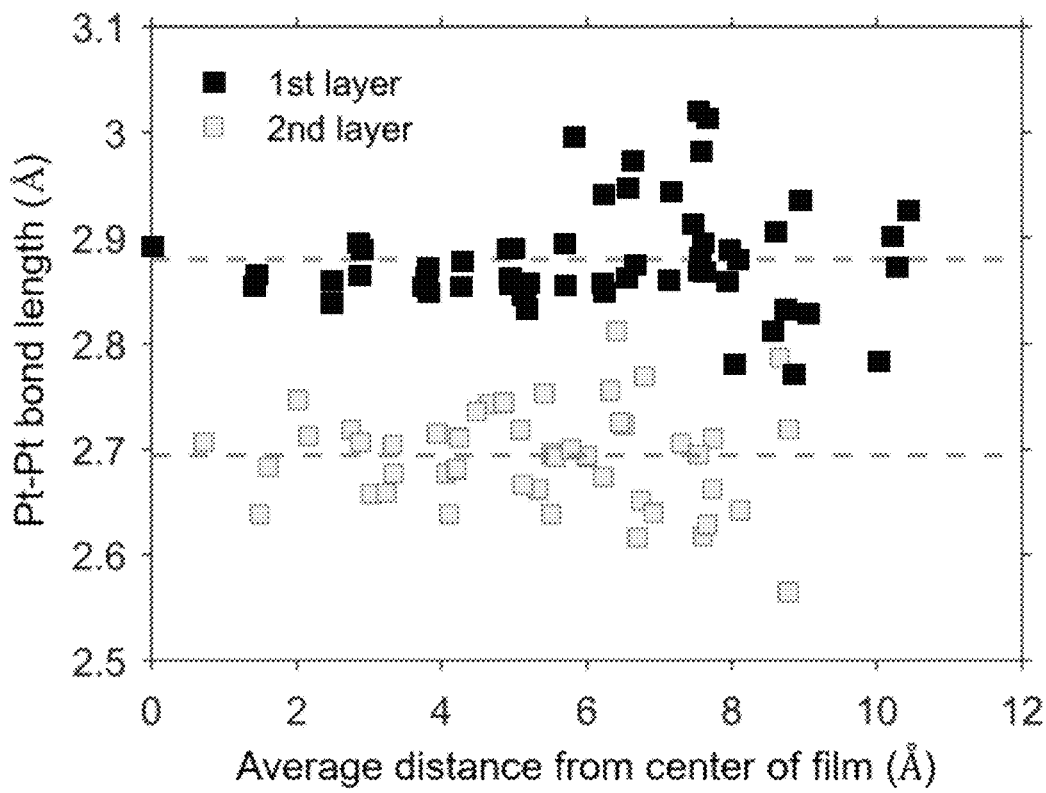
FIG. 17. Average Pt—Pt bond distances for Pt atoms on different layers.

For the first layer of Pt, our DFT calculations show a distorted Pt (110) interplanar spacing (2.87 Å) is expanded to match the a lattice parameter (2.94 Å) of the optimized MXene substrate (FIG. 16). This indicates that the strong anchoring of Pt atoms at the C hollow sites can overcome the metallic bonding among the Pt atoms, which results in strained Pt monolayers. Moreover, our DFT calculation also indicate that the Pt—Pt bond distance of monolayers is in asymmetric environments: Pt atoms near the center of the Pt monolayer are exactly situated on hcp sites (topmost C atoms), while the Pt atoms near the edge have higher or lower Pt—Pt bond lengths (FIG. 17). For the second layer of Pt, however, the average Pt—Pt bond distance is significantly shortened to 2.69 Å, indicating that the $Mo_2TiC_2T_x$ MXene has less impact on the Pt layers that are not in direct contact with the support and that the metal-support interfaces play pivot roles in Pt—Pt bond distances. Our DFT calculations shows that the average Pt—Pt bond distance of the first and second nanolayers is 2.78 Å, which is in good agreement with the results of in situ X-ray absorption spectroscopy (2.79 Å). Both of our experiments and theoretical calculations indicate that Pt nanolayers are strained with expanded average interplanar distances due to the $Mo_2TiC_2T_x$ support.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A catalyst comprising an MXene support of Formula I:

$$M_{n+1}X_nT_x \quad (I);$$

wherein
   each M is independently an early transition metal;
   X is a non-metal wherein the non-metal is carbon or nitrogen;
   $T_x$ is a surface functional group wherein x is 0-10; and n is 1, 2, or 3; and
   a noble metal wherein atoms of the noble metal occupy crystal lattice nodes at the basal plane of the MXene support, and the atoms of the noble metal are supported by a metallic bond to the early transition metal;
   wherein the noble metal has one to five nanostructured layers of its atoms on the MXene support, and loading of the noble metal on the MXene support is less than 5 weight percent based on the catalyst.

2. The catalyst of claim 1 wherein the occupied crystal lattice node is a hexagonal close packed (HCP) crystal lattice node.

3. The catalyst of claim 1 wherein the non-metal occupies a crystal lattice node between the early transition metal and a different second early transition metal that occupies another crystal lattice node.

4. The catalyst of claim 3 wherein the noble metal has one, two, or three nanostructured layers of its atoms on the MXene support.

5. The catalyst of claim 3 wherein the catalyst has a surface area of about 20 m²/g to about 40 m²/g, a pore size of about 0.5 nm to about 5 nm, and a pore volume of about 0.02 cm³/g to about 0.1 cm³/g.

6. The catalyst of claim 1 wherein the noble metal has one or two nanostructured layers of its atoms on the MXene support.

7. The catalyst of claim 1 wherein the one to five nanostructure layers of the noble metal has an average thickness of about 0.3 nanometers.

8. The catalyst of claim 1 wherein the loading is about 0.1 weight percent to about 2.5 weight percent.

9. The catalyst of claim 1 wherein the noble metal is platinum, iridium, rhodium, palladium, or a combination thereof.

10. The catalyst of claim 1 wherein M is hafnium, niobium, molybdenum, titanium, tungsten, tantalum, vanadium, zirconium, or a combination thereof.

11. The catalyst of claim 1 wherein x is 1-10 and the surface functional group is halo, hydroxyl, oxo, or a combination thereof.

12. The catalyst of claim 1 wherein X is carbon and n is 1 or 2.

13. The catalyst of claim 1 wherein the MXene support is $Mo_2TiC_2T_x$.

14. The catalyst of claim 1 wherein the catalyst is about 0.1 wt % to about 2 wt % of Pt loaded on a $Mo_2TiC_2T_x$ support.

15. The catalyst of claim 14 wherein a platinum atom is adjoining another platinum atom, the platinum atom and the adjoining platinum atom occupy HCP crystal lattice nodes at the basal plane of the MXene support, the platinum atom and the adjoining platinum atom are each supported by a metallic bond to a molybdenum atom, a carbon atom occupies another crystal lattice node between the molybdenum atom and a titanium atom that occupies a third crystal lattice node, and the carbon atom is positioned beneath the molybdenum atom.

16. The catalyst of claim 1 wherein the noble metal is a rhombic pattern of platinum atoms.

17. A method for converting methane to a hydrocarbon comprising contacting the catalyst according to claim 1 and methane at a temperature greater than 200° C., wherein the methane is converted to a saturated or unsaturated $C_2$-$C_8$ hydrocarbon.

18. The method of claim 17 wherein the catalyst is about 0.1 wt % to about 2 wt % of Pt loaded on a $Mo_2TiC_2T_x$ support.

19. The method of claim 17 wherein the contacting is at a gas hourly space velocity (GHSV) of about 4 h$^{-1}$ to about 14 h$^{-1}$ and at a temperature of about 600° C. to about 900° C.

20. A catalyst comprising an MXene support represented by the Formula:

$$Mo_2TiC_2T_x;$$

wherein $T_x$ is a surface functional group wherein x is 0-10; and
platinum metal wherein atoms of the platinum metal occupy crystal lattice nodes at the basal plane of the MXene support, and the atoms of the platinum metal are supported by a metallic bond to a molybdenum atom of the MXene support;
wherein the platinum metal has one or two nanostructured layers of its atoms on the MXene support; and loading of the platinum metal on the MXene support is less than 5 weight percent based on the catalyst.

* * * * *